(12) United States Patent
Therien et al.

(10) Patent No.: US 7,445,845 B2
(45) Date of Patent: Nov. 4, 2008

(54) SYNTHESIS, SPECTROSCOPY, PHOTOPHYSICS OF MULTI-CHROMOPHORIC ZN(II) GROUP 8 METAL COMPLEXES

(75) Inventors: Michael J. Therien, Philadelphia, PA (US); Harry Tetsuo Uyeda, College Park, MD (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 205 days.

(21) Appl. No.: 10/403,387

(22) Filed: Mar. 28, 2003

(65) Prior Publication Data

US 2004/0152826 A1 Aug. 5, 2004

Related U.S. Application Data

(60) Provisional application No. 60/368,493, filed on Mar. 28, 2002.

(51) Int. Cl.
*C07B 47/00* (2006.01)
*C07D 487/22* (2006.01)

(52) U.S. Cl. .................. 428/411.1; 327/527; 540/145; 514/185

(58) Field of Classification Search ............... 540/145; 514/185, 410; 568/910; 428/411.1; 327/524; 427/331
See application file for complete search history.

(56) References Cited

U.S. PATENT DOCUMENTS

| 5,064,264 A | 11/1991 | Ducharme et al. ........... 385/130 |
| 5,371,199 A | 12/1994 | Therien et al. ............... 534/11 |
| 5,493,017 A | 2/1996 | Therien et al. ............... 540/145 |
| 5,741,442 A | 4/1998 | McBranch et al. ........... 252/582 |
| 5,756,723 A | 5/1998 | Therien et al. ............... 540/145 |
| 5,783,306 A * | 7/1998 | Therien et al. ............ 428/411.1 |
| 5,986,090 A | 11/1999 | Therien et al. ............... 540/145 |
| 6,067,186 A | 5/2000 | Dalton et al. ................ 359/321 |
| 6,090,332 A | 7/2000 | Marder et al. ................ 264/435 |
| 6,348,992 B1 | 2/2002 | Zhang et al. ................. 359/321 |

OTHER PUBLICATIONS

Therien et al., JACS 1993, vol. 115, pp. 2513-2515.*
Burland et al., Chem. Rev., 94:31 (1994).
DiMagno et al., J. Org. Chem., 58:5983 (1993).
DiMagno et al., J. Org. Chem., 59:6943 (1994).
DiMagno et al., J. Am. Chem. Soc., 115:2513 (1993).
Karki et al., J. Am. Chem. Soc., 120:2606 (1998).
LeCours et al., J. Am. Chem. Soc., 119:12578 (1997).
LeCours et al., J. Am. Chem. Soc., 118:1497 (1996).
Lin et al., Science, 264:1105 (1994).
Priyadarshy et al, J. Am. Chem. Soc., 118:1504 (1996).
Uyeda et al., J. Am. Chem. Soc., 124:13806-13813 (2002).

* cited by examiner

*Primary Examiner*—Robert D. Harlan
(74) *Attorney, Agent, or Firm*—Fox Rothschild LLP

(57) ABSTRACT

Novel multichromophoric complexes comprising the formula

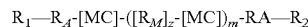

are provided. Polymeric compositions and devices comprising the same are also discussed. The complexes are characterized by a central bridging moiety comprising one or a plurality of linked conjugated macrocyclic molecules [MC] coupled to at least one inorganic moiety ($R_1$ and/or $R_2$) through organic linker $R_4$. Preparation methods include metal-mediated cross-coupling techniques. The complexes can be useful in nonlinear optical devices and other optoelectronic applications.

110 Claims, 18 Drawing Sheets

SYNTHESIS, SPECTROSCOPY, PHOTOPHYSICS OF MULTI-CHROMOPHORIC ZN(II) GROUP 8 METAL COMPLEXES

RELATED APLICATION DATA

The present application claims priority benefit under 35 U.S.C. §119(e) of U.S. Provisional Patent Application Ser. No. 60/368,493 filed Mar. 28, 2002, the disclosure of which is incorporated herein by reference it its entirety.

GOVERNMENT SUPPORT

The research disclosed herein was supported by the Office of Naval Research (N00014-98-1-0725).

FIELD OF THE INVENTION

The present invention relates to novel polynuclear metal complexes, and more particularly, to porphyrin-based multi-chromophores having applications in the field of optoelectronics. The present invention further relates to polymers and their synthesis, as well as non-linear optical (NLO) and optoelectronic devices comprising these novel polynuclear metal complexes.

BACKGROUND OF THE INVENTION

Future generations of optoelectronic devices for telecommunications, information storage, external generation photoelectric devices, optical switching, and signal processing are predicated to a large degree on the development of materials with large nonlinear optical (NLO) responses. Toward this end, considerable effort has been directed to elucidating the chromophore design elements that correlate most closely with large first-order hyperpolarizabilities. This is due to the fact that an NLO chromophore with a high molecular first hyperpolarizability would be a highly desirable candidate for incorporation into ordered polymeric systems, and thus serve as the basis for macroscopic materials for frequency doubling as well as optoelectronic devices that function as waveguide switches, modulators, filters, and polarization transformers.

Design, modification, and further fine-tuning of the magnitude of the molecular first hyperpolarizability ($\beta_{(0)}$) of a given chromophore has generally been thought of in the context of Oudar's two-state model:

$$(\beta_{(0)}) \propto (\mu_{ee} - \mu_{gg}) \mu_{ge}^2 / E_{ge}^2 \quad (1)$$

where g and e represent the indices of the ground and charge transfer (CT) excited states, respectively; $\mu$ is the dipole matrix element; and E is the transition energy.

Most NLO chromophores are composed of an electron donor (D) and an electron acceptor (A), the molecular entities chiefly involved in charge redistribution, as well as a bridge (i.e., the molecular scaffolding that links the D and A portions of the chromophore). To date, the design of chromophores with good second-order nonlinear properties has focused primarily on engineering: (i) the electronic nature of the D and A, and (ii) the conjugation length of the bridge. The former controls D-A mixing with respect to a specific bridge, while the latter plays a role in modulating D-A electronic coupling and also determines the magnitude of the change in dipole moment. Per Equation (1), increasing the bridge conjugation length increases the magnitude of the change of dipole moment, while concomitantly diminishing the square of the dipole matrix element and increasing the square of the CT transition energy; the latter two effects have their genesis in the fact that increased bridge lengths attenuate D-A electronic coupling. Maximizing $\beta_{(0)}$ thus involves an interplay between three parameters that do not necessarily simultaneously attain their optimal value for a particular molecular structure (D, A, bridge).

Most of the chromophores that have been studied to date for their second-order nonlinear properties can be classified as D-A systems in which the molecular bridge is based either on ethene, phenylene, ethyne, small-ring heteroaromatic, styrene building blocks, or a combination of two or more of these simple units. Although a variety of different organic media have been utilized as D-A bridging moieties, comparatively little attention has been paid to how the details of the bridge topology and electronic structure impact the chromophore second-order NLO response, particularly when viewed alongside the body of literature describing how D-A electronic properties and bridge length modulate the molecular first hyperpolarizability.

Engineering of bridge electronics and topology has been a primary focus in developing new classes of NLO chromophores with exceptional photophysical properties. A basic criterion is that the bridge should be much more polarizable than the simple polyene, polyyne, polyphenylene, and polyheteroaromatic structures that have been most commonly used. Ideally, the bridge-localized excited state should dramatically alter D-A electronic coupling relative to the coupling the ground-state bridge provides.

One approach to enabling such differential ground- and excited-state coupling is to choose a D-A bridging motif that is capable of accessing a resonance form in its excited state that is unattainable for the ground-state structure. Such an excited-state resonance structure would be optimal if it produced a large transition dipole oriented directly along the D-to-A molecular charge transfer axis. A designed excited state with these properties would facilitate large molecular first hyperpolarizabilities since the magnitude of the change in dipole moment would not be held ransom by significant diminution of the oscillator strength of the CT transition or an increase in the transition energy at relatively large D-A distances, since a high oscillator strength, bridge-centered transition would now directly couple D to A. Presumably, if the orientation and dipolar nature of the bridge-centered CT transition could be maintained over a long range in such a system, $\mu_{ee} - \mu_{gg}$ and $\mu_{ge}^2$ would simultaneously increase with augmented bridge lengths while concomitantly maintaining or slightly reducing $E_{ge}^2$.

Exemplifying some of the desired properties of NLO chromophores discussed above are the so-called push-pull arylethynyl porphyrin systems described in U.S. Pat. No. 5,783, 306; LeCours, et al., *J. Am. Chem. Soc.*, 1996, 118, 1497; Priyadarshy, et al., *J. Am. Chem. Soc.*, 1996, 118, 1504; LeCours, et al., *J. Am. Chem. Soc.*, 1997, 119, 12578; and Karki, et al., *J. Am. Chem. Soc.*, 1998, 120, 2606. These compounds, which contain organic donor/acceptor groups connected through a porphyrin-based bridging system, exhibit remarkably large molecular first-order hyperpolarizabilities. In addition to very large molecular first hyperpolarizabilities, chromophores for optoelectronic applications often require thermal stabilities in excess of 200° C. Thus, new compounds are needed that show both large hyperpolarizabilities and greater thermostability. The compounds, compositions, devices, and methods of the present invention address these and other needs.

SUMMARY OF THE INVENTION

The present invention provides compounds having Formula I:

$$R_1-R_A\text{-}[MC]\text{-}([R_M]_z\text{-}[MC])_m\text{-}R_A-R_2 \qquad \text{I}$$

wherein: each MC is, independently, a conjugated macrocycle; each $R_A$ is, independently, a covalent bond, alkenyl having 2 to about 20 carbon atoms, cumulenyl having 4 to about 14 carbon atoms, or alkynyl having 2 to about 20 carbon atoms; each $R_M$ is, independently, alkyl having 1 to about 20 carbon atoms, alkenyl having 2 to about 20 carbon atoms, cumulenyl having 4 to about 14 carbon atoms, alkynyl having 2 to about 20 carbon atoms, aryl having 3 to about 50 carbon atoms, arylalkynyl having 8 to about 24 carbon atoms, arylalkenyl having 8 to about 24 carbon atoms, unsaturated heterocyclo having 4 to about 24 carbon atoms, heteroaryl having 2 to about 50 carbon atoms, unsaturated heterocycloalkenyl, unsaturated heterocycloalkynyl or heteroarylalkynyl; $R_1$ is H, halo, a protecting group, an organic electron donor group or an inorganic electron donor moiety, and $R_2$ is H, halo, a protecting group, an organic electron acceptor group or an inorganic electron acceptor moiety, wherein at least one of $R_1$ and $R_2$ is an inorganic moiety comprising an organic ligand; m is 0 to about 50; and z is 0 or 1.

The present invention further provides compounds having Formula II or III

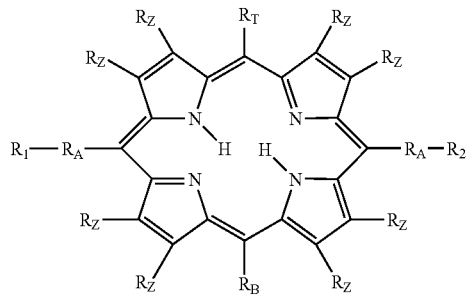

II

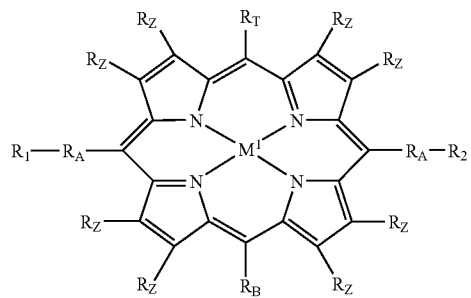

III wherein: $M^1$ is a metal atom; each $R_A$ is, independently, a covalent bond, alkenyl having 2 to about 20 carbon atoms, cumulenyl having 4 to about 14 carbon atoms, or alkynyl having 2 to about 20 carbon atoms; $R_1$ is H, halo, a protecting group, an organic electron donor group or an inorganic electron donor moiety; and $R_2$ is H, halo, a protecting group, an organic electron acceptor group or an inorganic electron acceptor moiety, wherein at least one of $R_1$ and $R_2$ is an inorganic moiety; each $R_T$ and $R_B$ is, independently, alkyl having 1 to about 20 carbon atoms, alkenyl having 2 to about 20 carbon atoms; alkynyl having 2 to about 20 carbon atoms, aryl having 3 to about 50 carbon atoms, arylalkynyl having 8 to about 24 carbon atoms, heteroaryl having 2 to about 50 carbon atoms, unsaturated heterocyclo having 4 to about 24 carbon atoms, unsaturated heterocycloalkenyl, or unsaturated heterocycloalkynyl, wherein each $R_T$ and $R_B$ is optionally substituted; and each $R_Z$ is, independently, H, an electron-donating group, or an electron-withdrawing group.

Further embodiments according to the present invention provide compounds having Formula IV or V

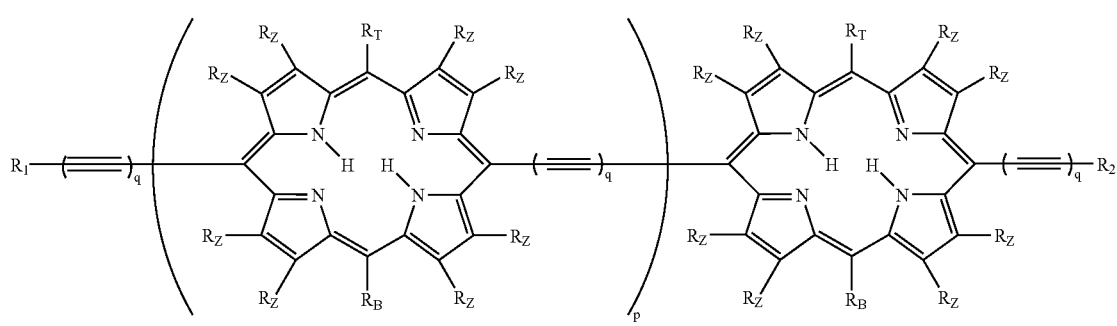

IV

-continued

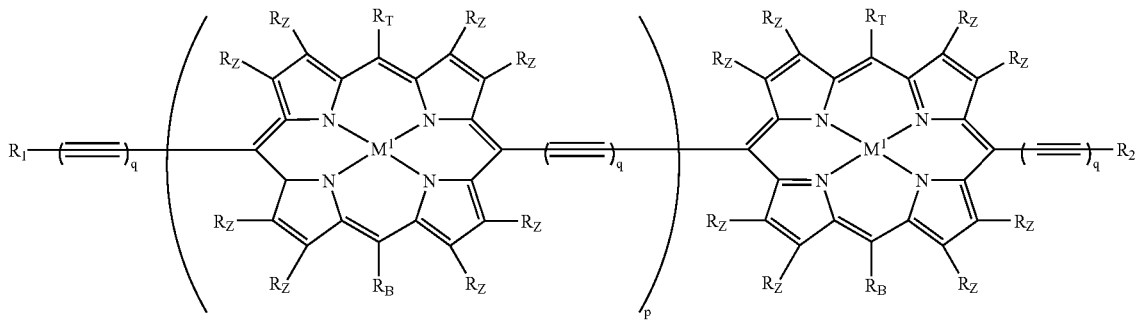

V wherein: $M^1$ is a metal atom; $R_1$ is H, halo, a protecting group, an organic electron-donating group or an inorganic electron donor moiety; and $R_2$ is H, halo, a protecting group, an organic electron acceptor group or an inorganic electron acceptor moiety, wherein at least one of $R_1$ and $R_2$ is an inorganic moiety each $R_T$ and $R_B$ is, independently, alkyl having 1 to about 20 carbon atoms, alkenyl having 2 to about 20 carbon atoms; alkynyl having 2 to about 20 carbon atoms, aryl having 3 to about 50 carbon atoms, arylalkynyl having 8 to about 24 carbon atoms, heteroaryl having 2 to about 50 carbon atoms, unsaturated heterocyclo having 4 to about 24 carbon atoms, unsaturated heterocycloalkenyl, or unsaturated heterocycloalkynyl wherein each $R_T$ and $R_B$ is optionally substituted; each $R_Z$ is, having 4 to about 24 carbon atoms, insaturated heterocycloalkenyl, or unsaturated heterocycloalkynyl, wherein each $R_T$ and $R_B$ is optionally substituted; each $R_Z$ is, independently, H, an electron-donating group, or an electron-withdrawing group; p is 0 to 50; and q is 1 to 5.

The present invention further includes processes for preparing the above-recited multichromophoric compounds.

Also provided are compositions comprising synthetic organic polymer and at least one of the above-recited multichromophoric compounds.

Further embodiments include devices comprising a substrate and at least one layer on the substrate, where the layer comprises a multichromophoric compound as recited above. Processes for preparing these devices, comprising the steps of providing a substrate and placing upon the substrate at least one layer, are also provided.

DESCRIPTION OF PREFERRED EMBODIMENTS

Figure 1:
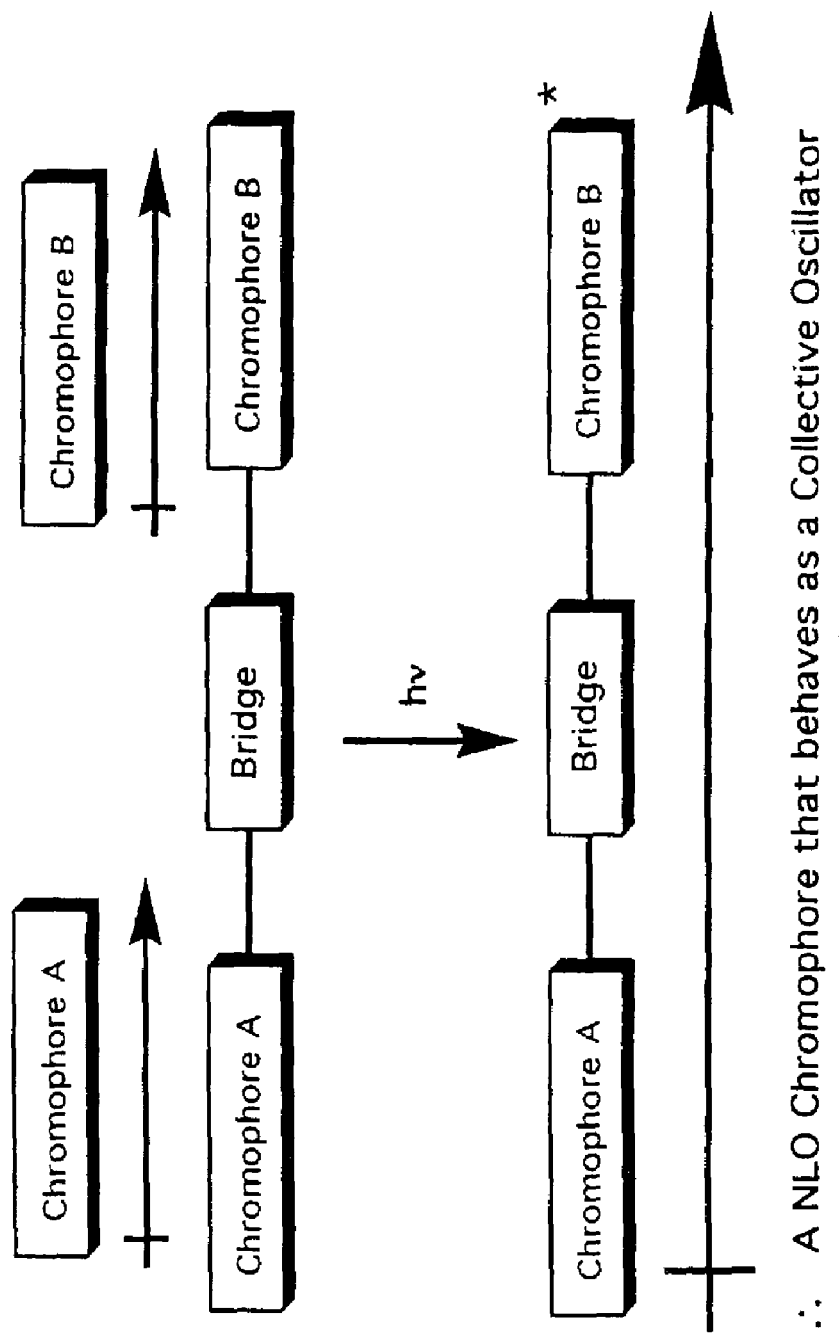
FIG. 1 shows a representation of multichromophoric compounds of the present invention.
Figure 2:
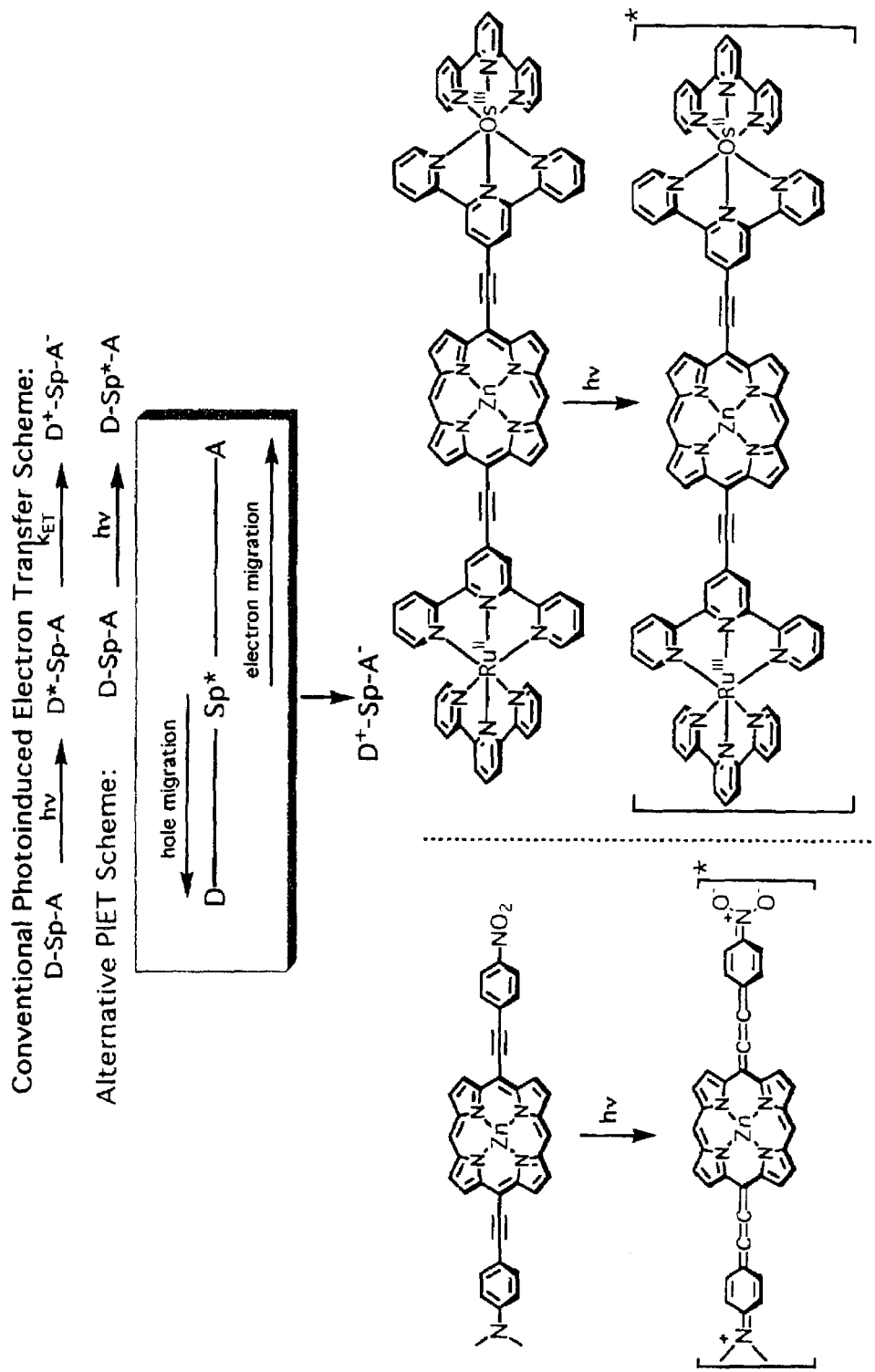
FIG. 2 illustrates ultrafast electron transfer (ET) using a photoexcitable spacer moiety in accordance with embodiments of the present invention.
Figure 3:
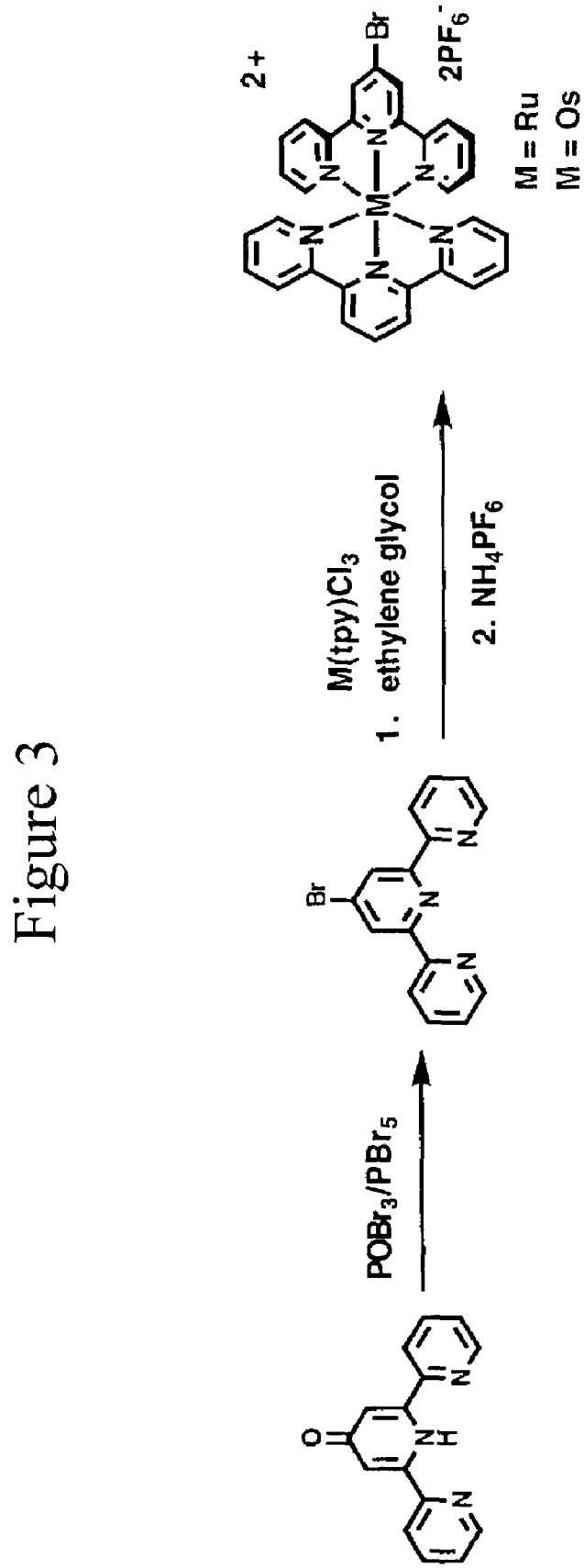
FIG. 3 shows a procedure for the preparation of intermediates used in the synthesis of multichomophoric compounds according to the present invention.
Figure 4:
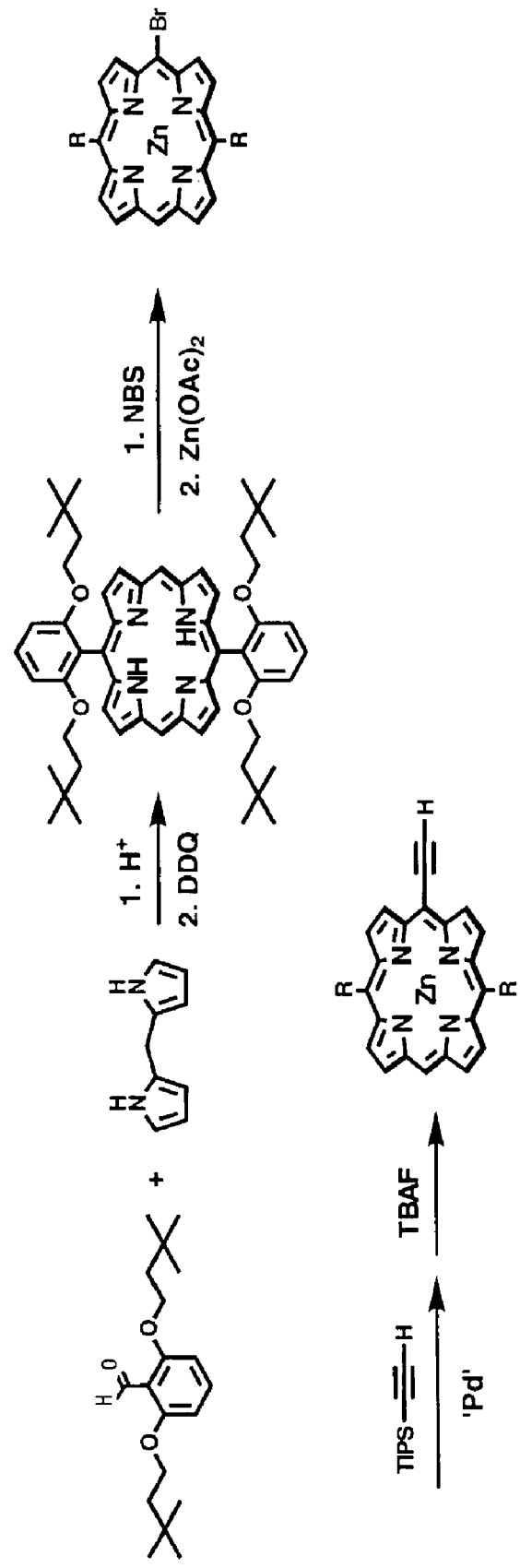
FIG. 4 shows a procedure for the preparation of conjugated macrocyclic intermediates useful in the synthesis of multichromophoric compounds according to the present invention.
Figure 5:
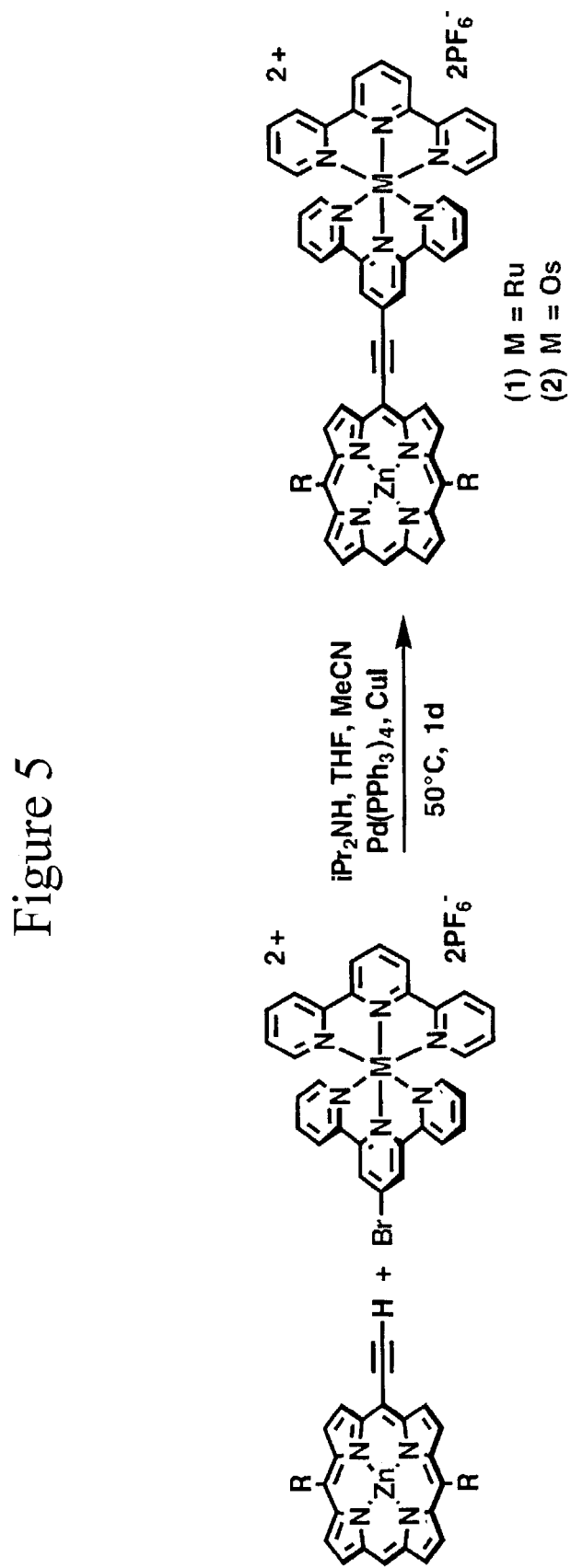
FIG. 5 shows a preparation of bis(chromophoric) compounds of the present invention.
Figure 6:
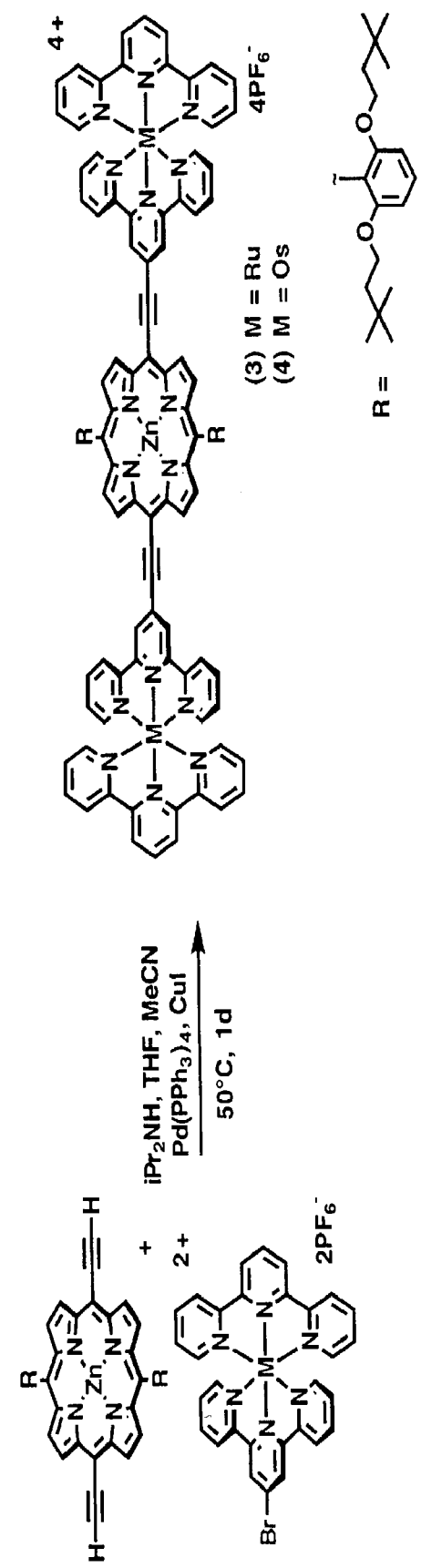
FIG. 6 shows a preparation of symmetric tris(chromophoric) compounds of the present invention.
Figure 7:
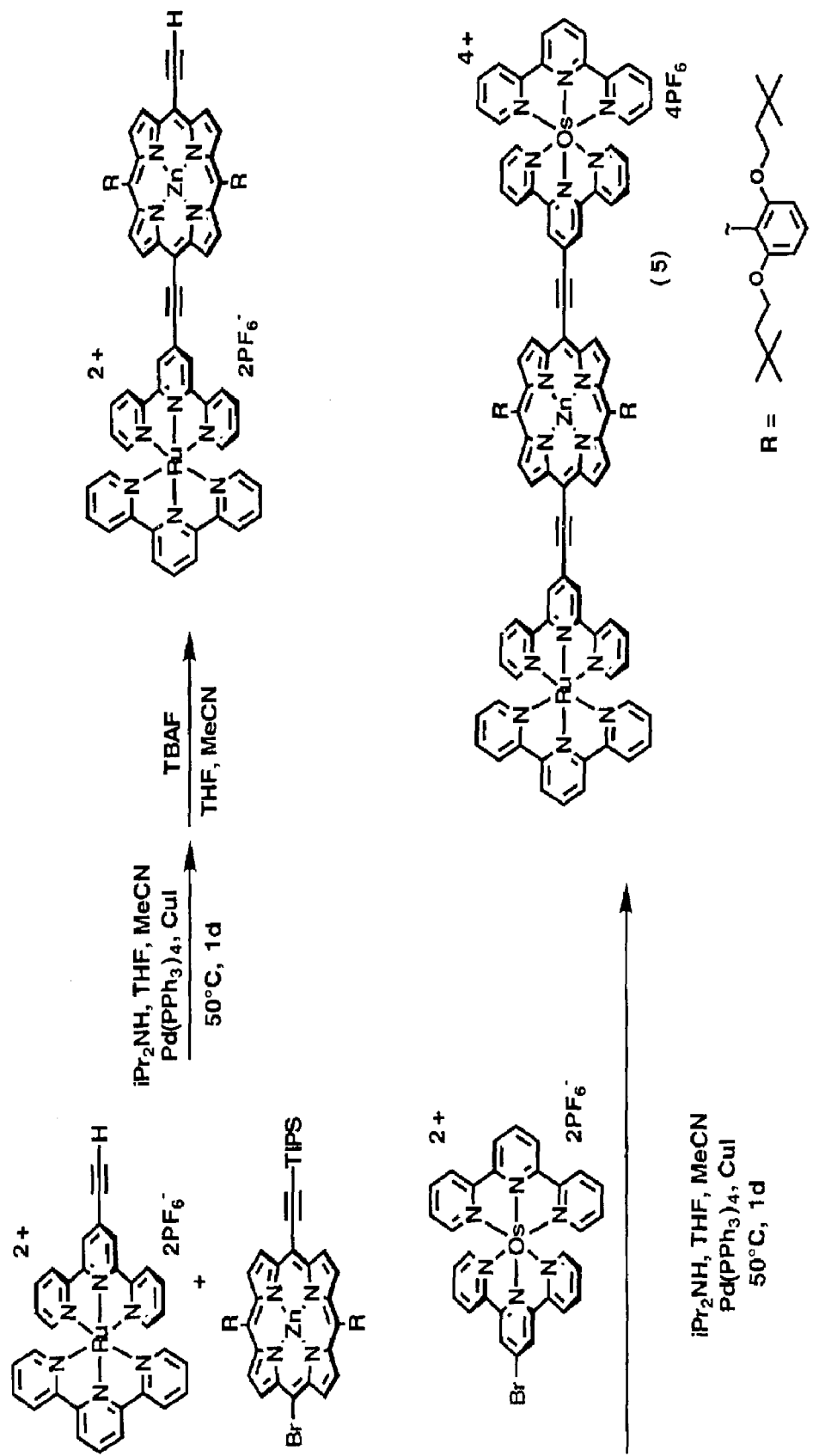
FIG. 7 shows a preparation of asymmetric tris(chromophoric) compounds of the present invention.
Figure 8:
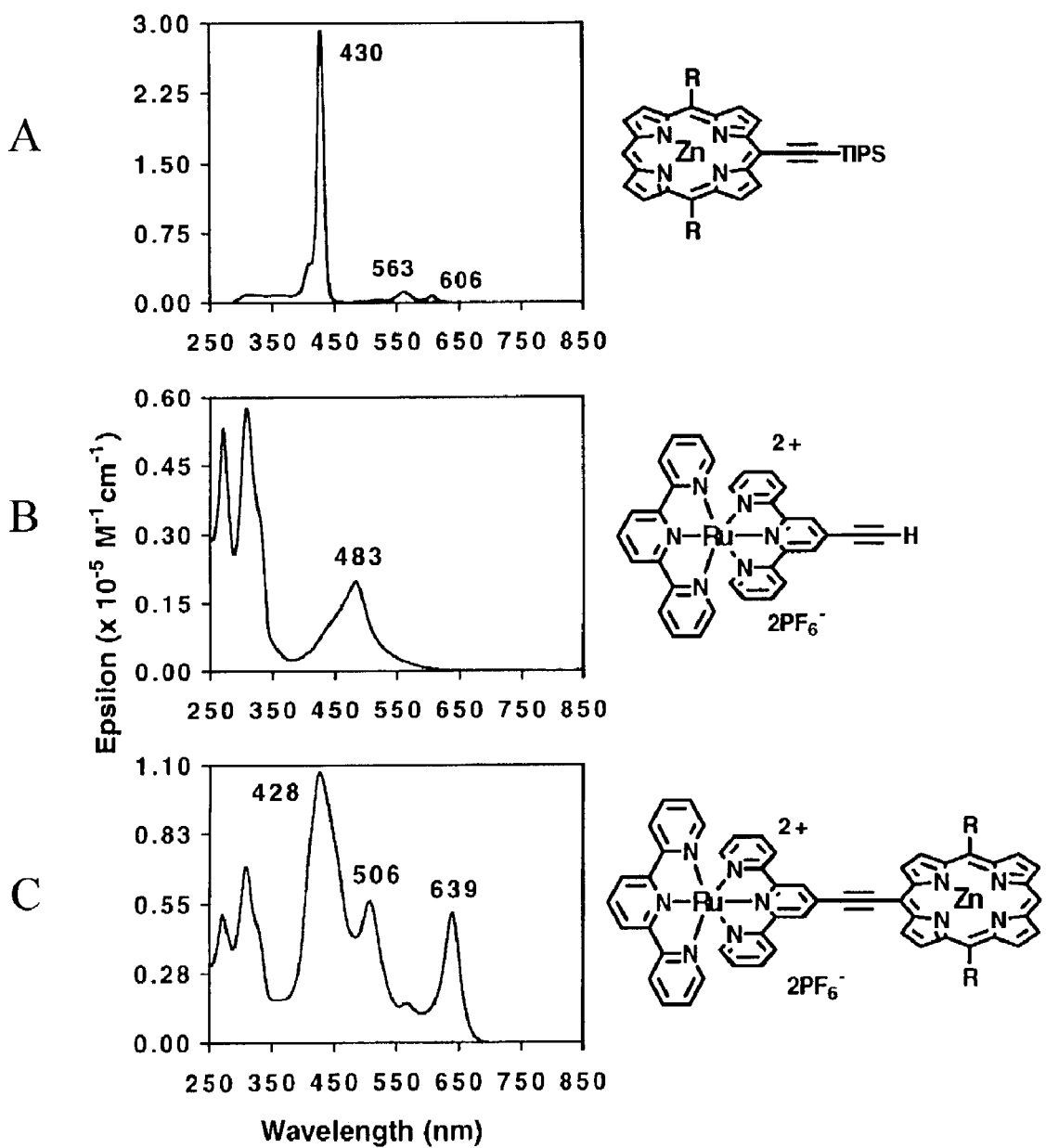
FIGS. 8A-8C compare electronic absorption spectra of a Ru-containing bis(chromophoric) compound and related chromophores.
Figure 9:
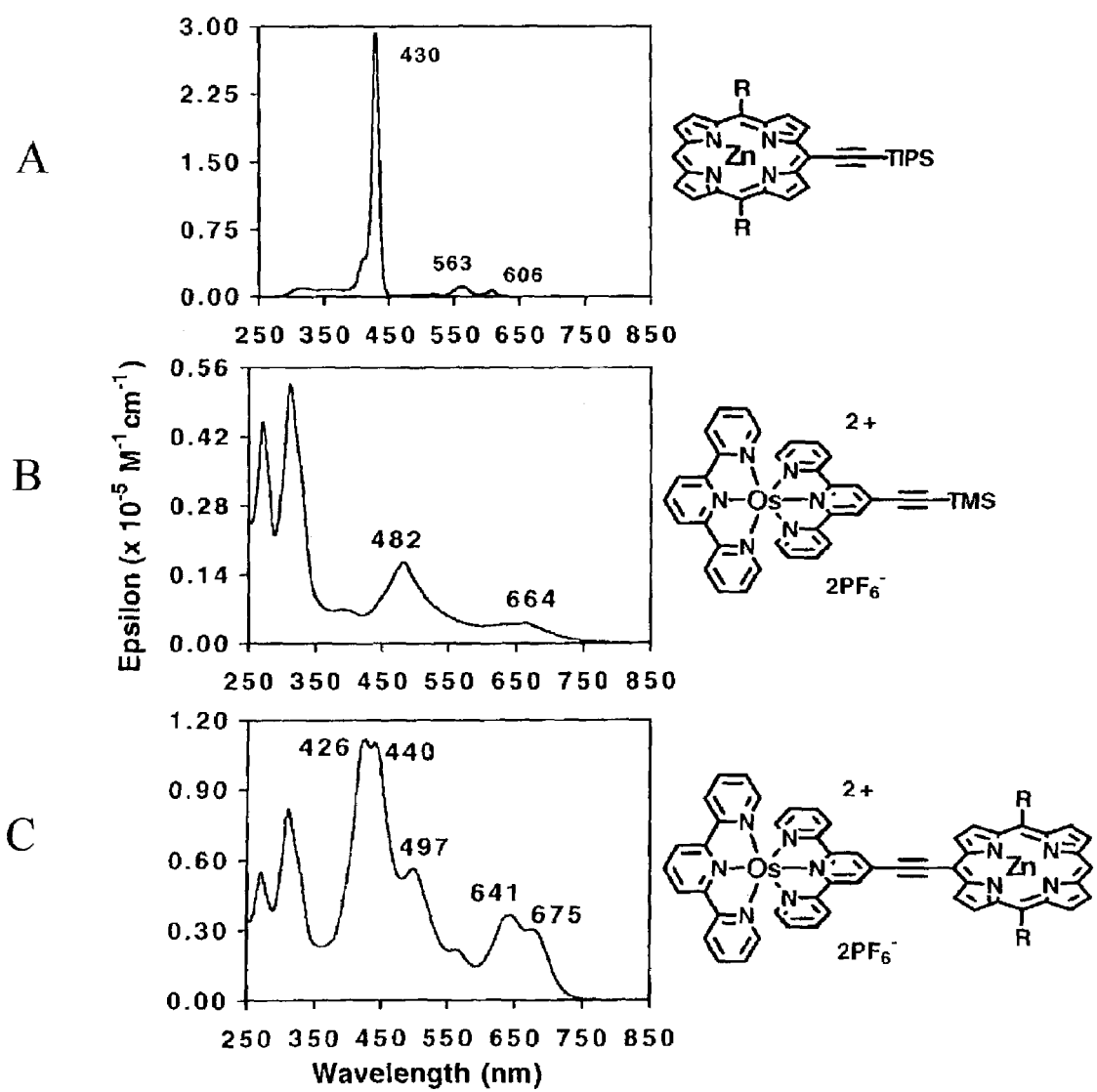
FIGS. 9A-9C compare electronic absorption spectra of an Os-containing bis(chromophoric) compound and related chromophores.
Figure 10:
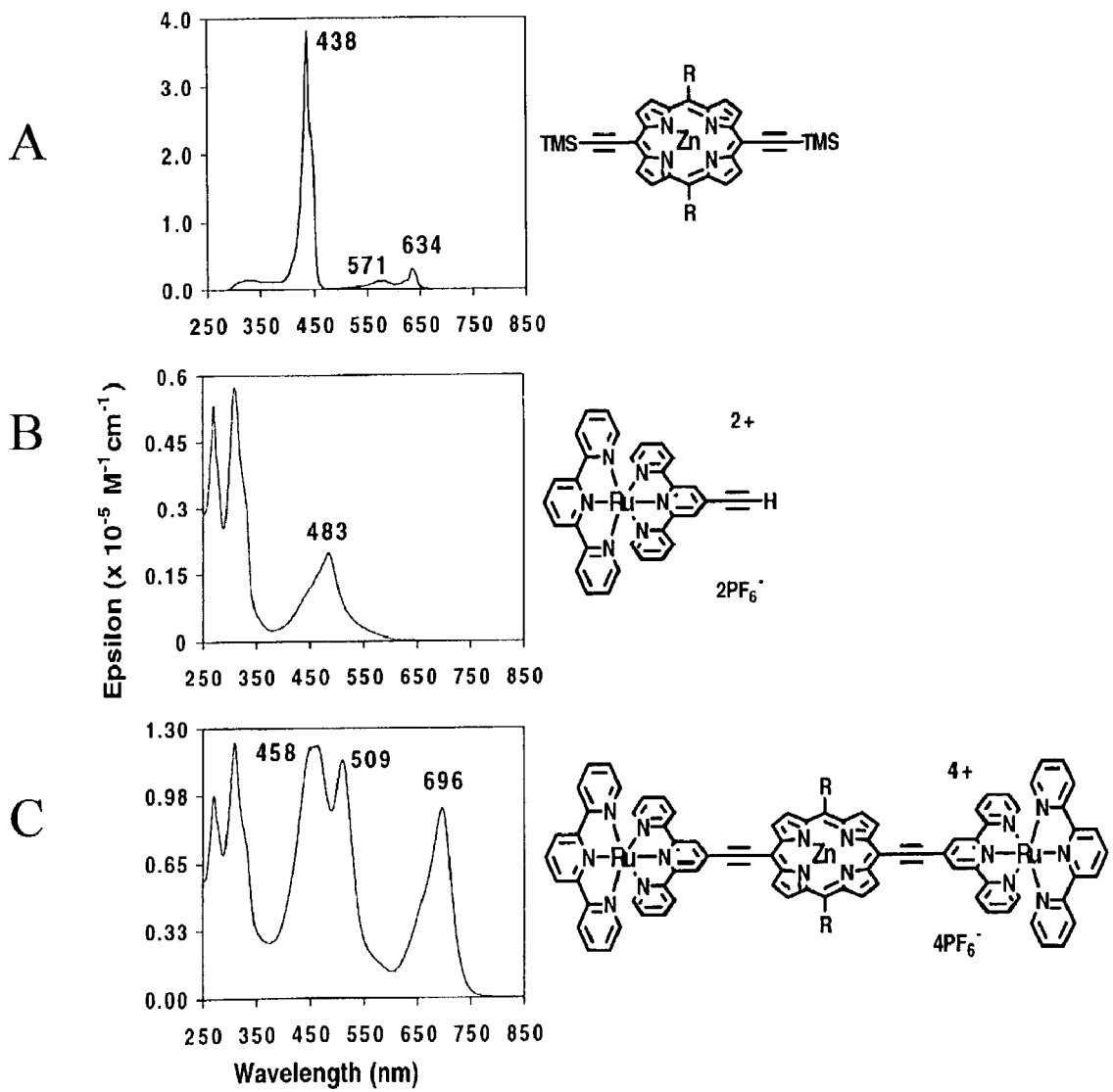
FIGS. 10A-10C compare electronic absorption spectra of a Ru-containing symmetric tris(chromophoric) compound and related chromophores.
Figure 11:
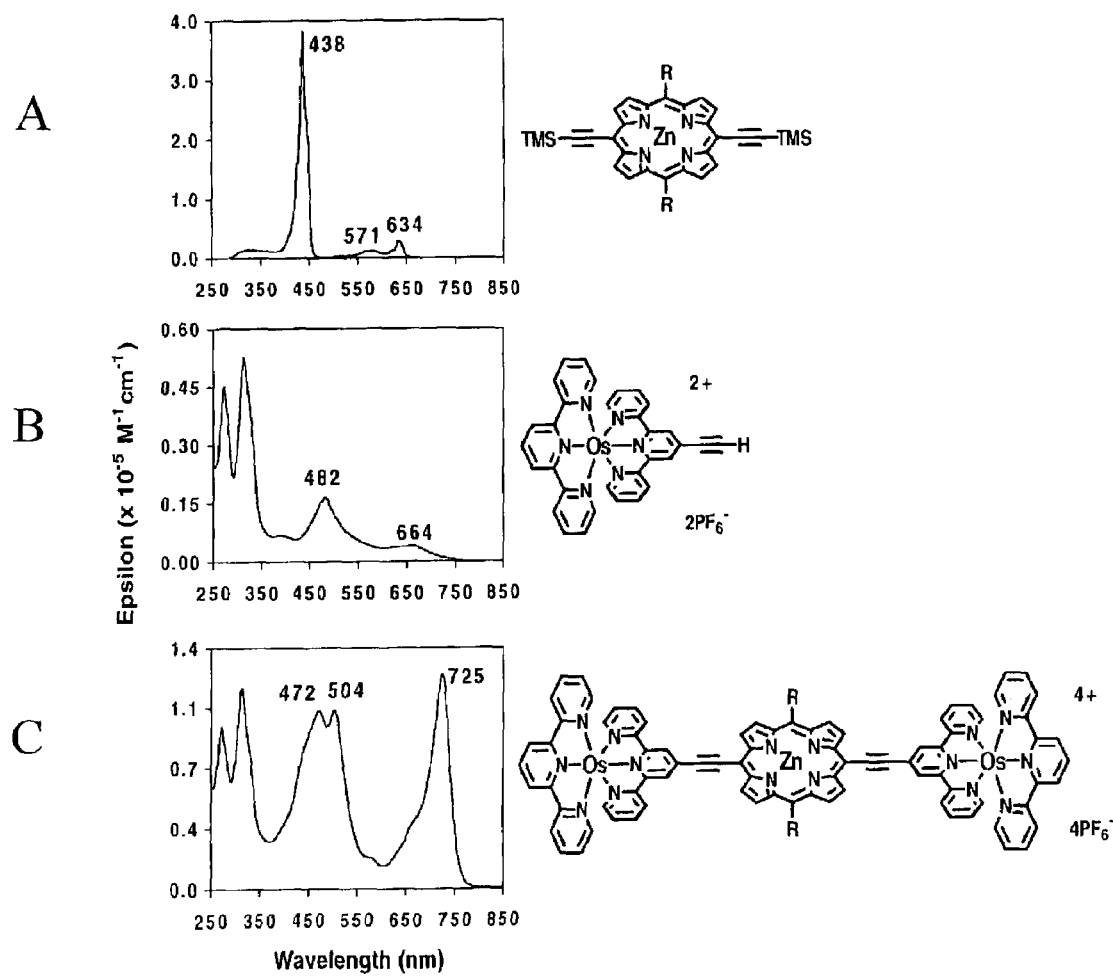
FIGS. 11A-11C compare electronic absorption spectra of an Os-containing symmetric tris(chromophoric) compound and related chromophores.
Figure 12:
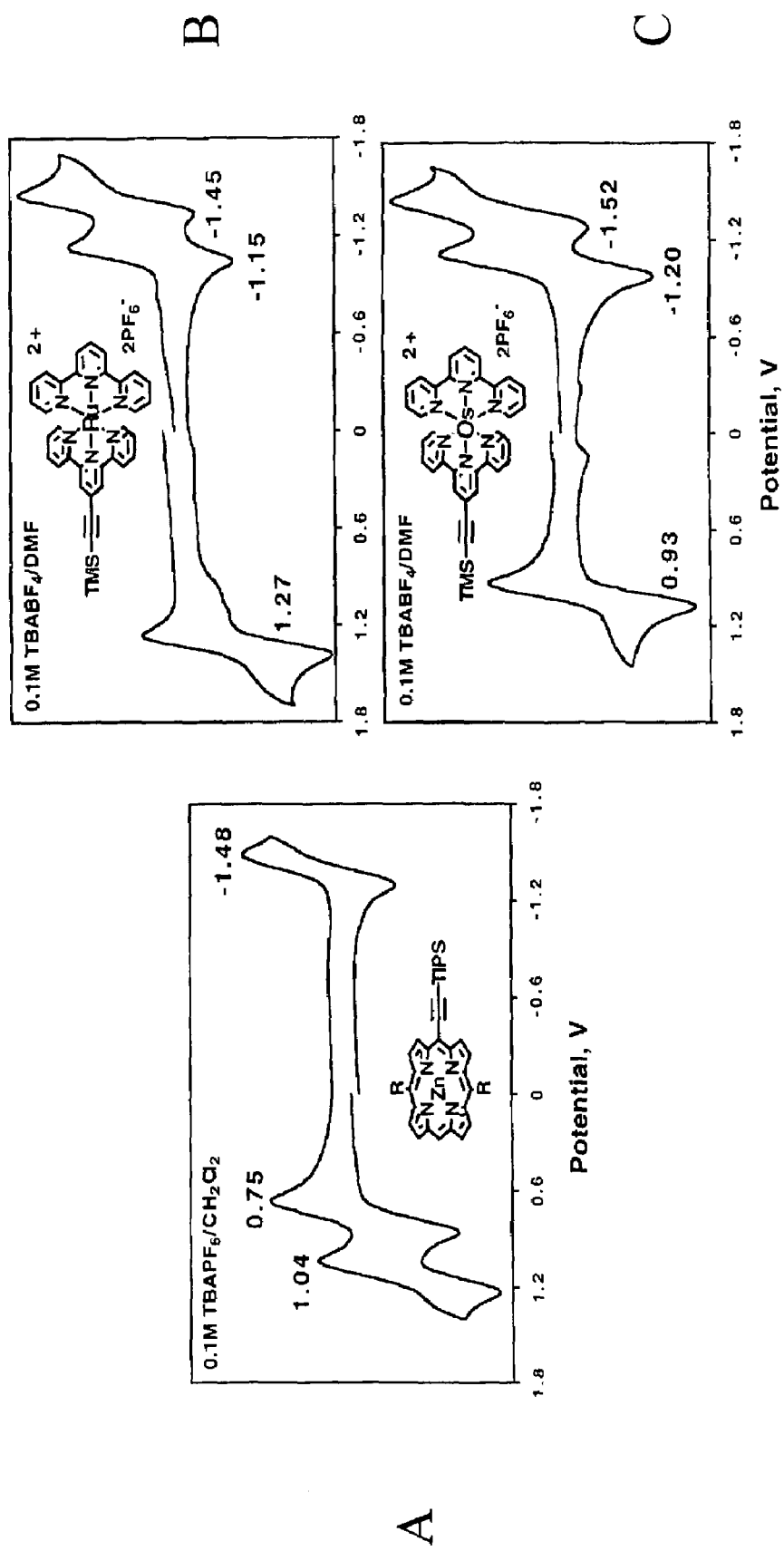
FIGS. 12A-12C show cyclic voltammetric responses obtained for certain compounds related to present invention.
Figure 13:
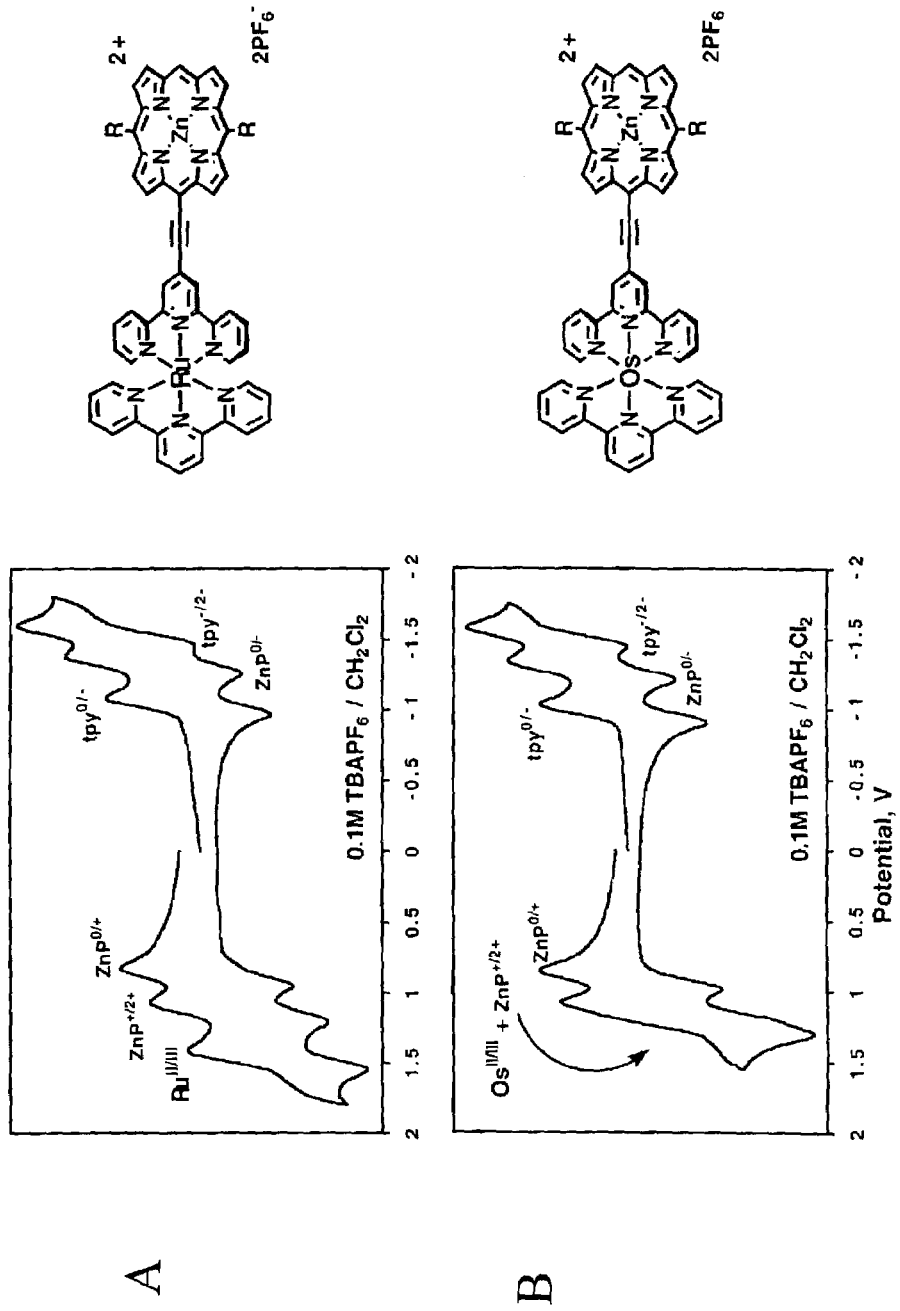
FIGS. 13A-13B show cyclic voltammetric responses obtained for certain bis(chromophoric) compounds of the present invention.
Figure 14:
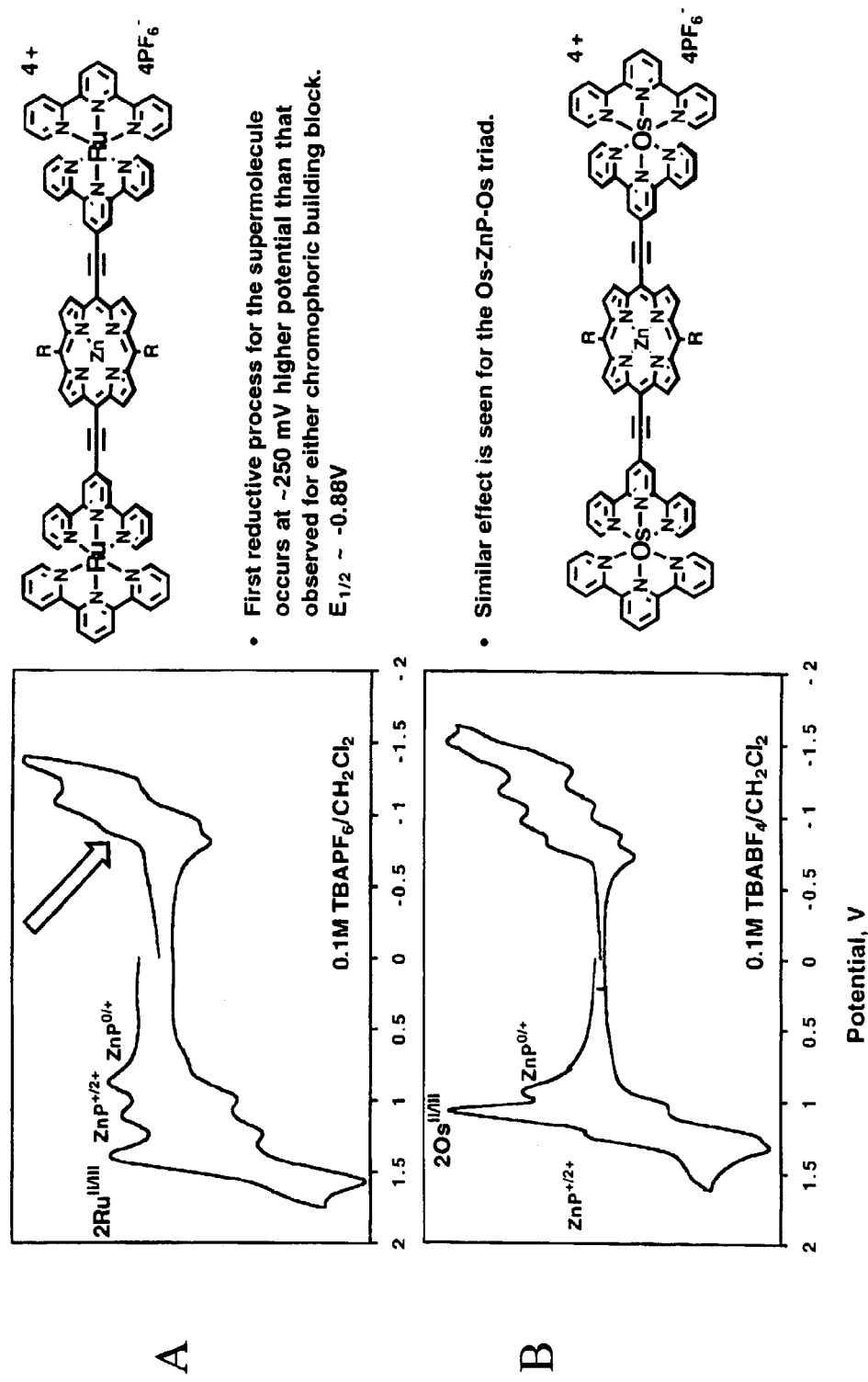
FIGS. 14A-14B show cyclic voltammetric responses obtained for certain tris(chromophoric) compounds of the present invention.
Figure 15:
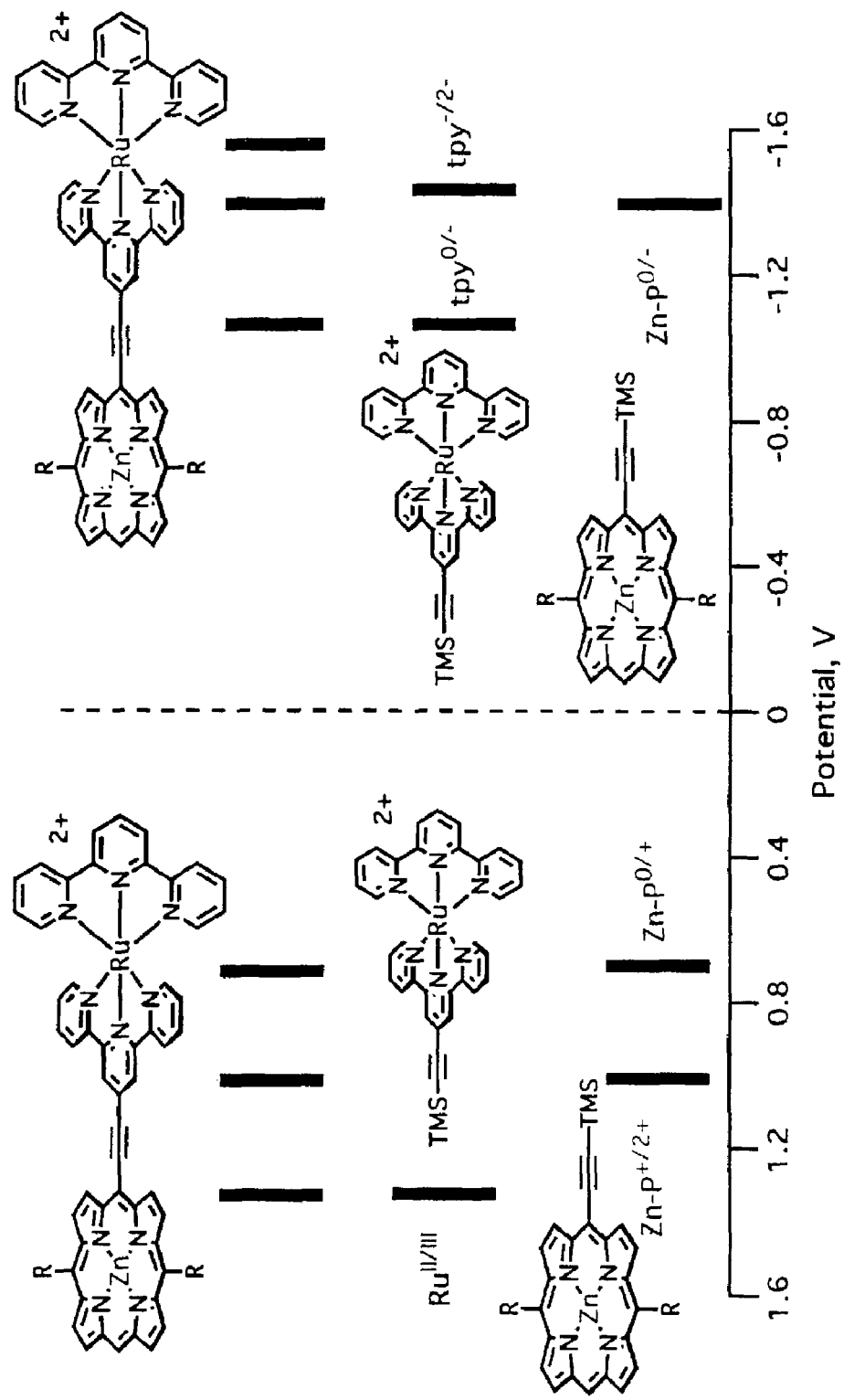
FIG. 15 compares electronic spectral properties of a bis(chromophoric) compound and related compounds.
Figure 16:
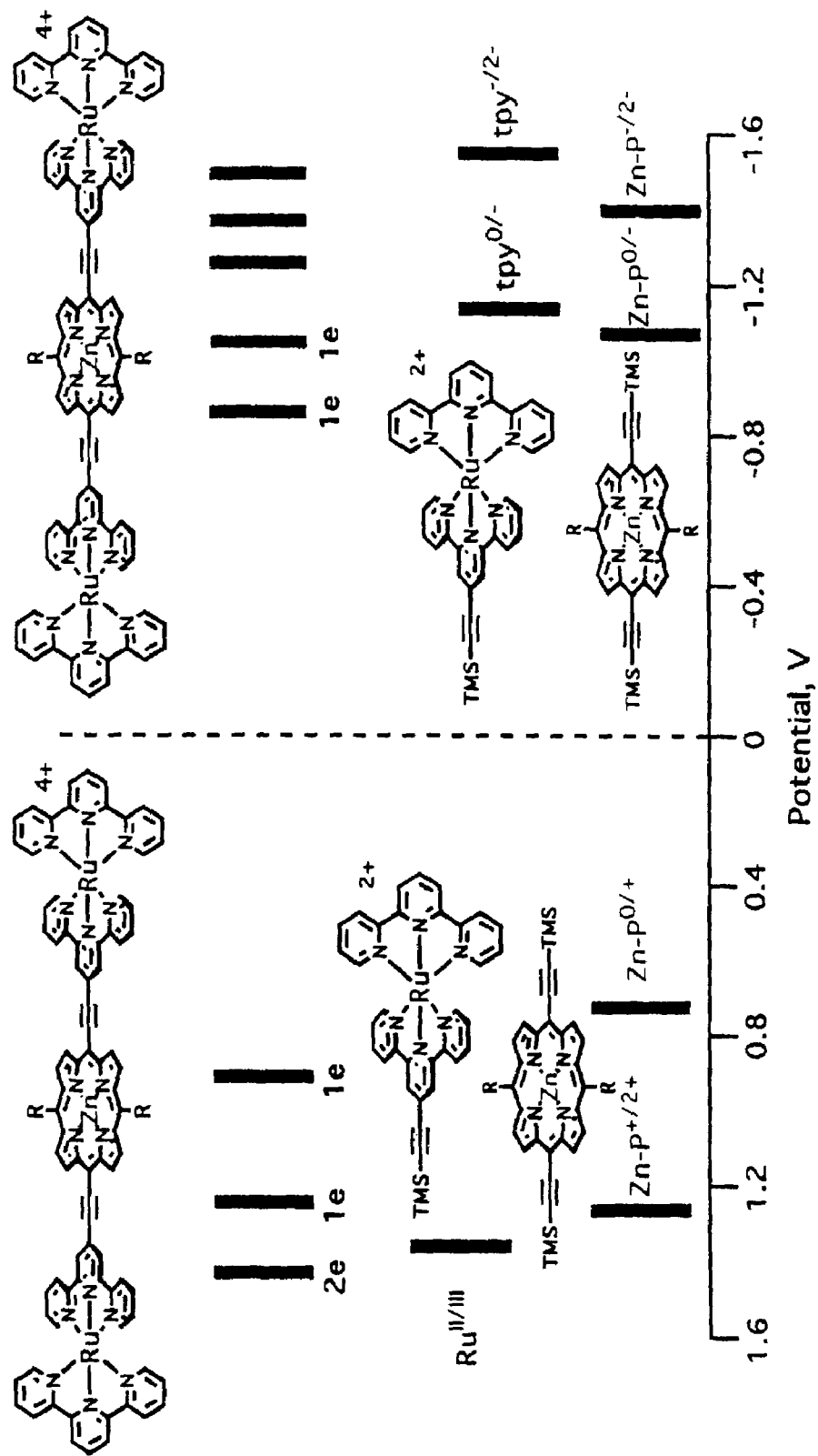
FIG. 16 compares electronic spectral properties of an asymmetric tris(chromophoric) compound and related compounds.
Figure 17:
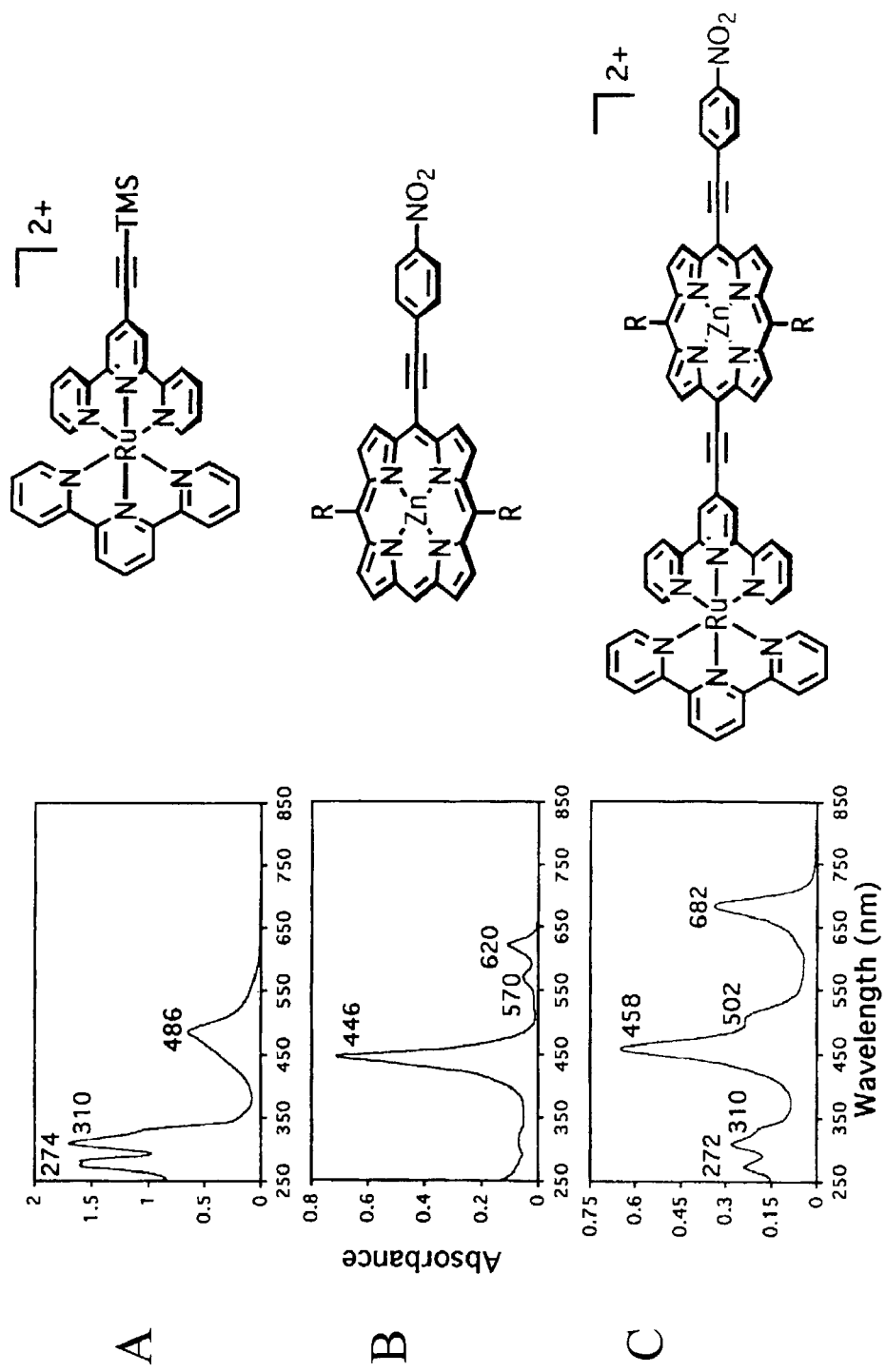
FIGS. 17A-17C compare electronic absorption spectra for compounds according to the present invention.

As used herein, the term "multichromophoric" is meant to refer to a molecular entity, charged or uncharged, comprising more than one chromophore component. "Chromophores" are molecules or chemical moieties capable of selective electromagnetic radiation absorption, particularly at the visible, UV, and NIR wavelengths. Such absorptions can be detected by electronic spectroscopy. Chromophores can be either organic or inorganic. Organic chromophores are typically characterized by extensive conjugation, while inorganic chromophores often include metal-ligand interactions. Multichromophoric compounds can contain any number of chromophores covalently joined together. Those containing two, three, or four chromophores are often referred to as diads, triads, tetrads, respectively, or bis(chromophoric) compounds, tris(chromophoric) compound, tetrakis(chromophoric) compounds, respectively.

The present invention includes, inter alia, multichromophoric compounds comprising Formula I:

$$R_1—R_A\text{-[MC]-}([R_M]_z\text{-[MC]})_m\text{-}R_A—R_2 \qquad I$$

wherein: MC is, independently, a conjugated macrocycle; each $R_A$ is, independently, a covalent bond, alkenyl having 2 to about 20 carbon atoms, cumulenyl having 4 to about 14 carbon atoms, or alkynyl having 2 to about 20 carbon atoms; each $R_M$ is, independently, alkyl having 1 to about 20 carbon atoms, alkenyl having 2 to about 20 carbon atoms, cumulenyl having 4 to about 14 carbon atoms, alkynyl having 2 to about 20 carbon atoms, aryl having 3 to about 50 carbon atoms, arylalkynyl having 8 to about 24 carbon atoms, arylalkenyl having 8 to about 24 carbon atoms, unsaturated heterocyclo having 4 to about 24 carbon atoms, heteroaryl having 2 to about 50 carbon atoms, unsaturated heterocycloalkenyl, or unsaturated heterocycloalkynyl; $R_1$ is H, halo, a protecting group, an organic electron donor group or an inorganic electron donor moiety; and $R_2$ is H, halo, a protecting group, an organic electron acceptor group or an inorganic electron acceptor moiety,. According to some embodiments, at least one of $R_1$ and $R_2$ is an inorganic moiety. In some embodiments, m is 0 to about 50 and z is 0 or 1. Compounds comprising Formula I can be charged or uncharged where charge is designated by the value n.

Conjugated macrocycles (MC) of Formula I function as polarizable bridging moieties serving to augment electronic coupling between attached donor and acceptor groups. As such, any cyclic or polycyclic molecule comprising a plurality of unsaturations manifest as double or triple bonds can be used as a conjugated macrocycle. In some embodiments, the conjugated macrocycles can be heterocylcic, comprising one or more heteroatoms. Some heterocyclic conjugated macrocycles include, but are not limited to, porphyrins, chlorins, phorbins, benzoporphyrins, bacteriochlorins, porphyrinogens, sapphyrins, texaphryins, and phthalocyanines, as well as N-confused versions of these species.

Conjugated macrocycles can also comprise one or more metal atoms such as, for example, transition metals, lanthanides, actinides, alkaline earth, and alkali metals. Further, any atom of the conjugated macrocycle that is not bound to groups $R_A$ or $R_M$ can bear substituents. These substituents, as well as any metal atom complexed to MC, can be chosen for their particular steric or electronic properties, for instance, to control intramolecular interactions and/or molecular order in the bulk phase as well as to influence ground state and excited state energy levels. Accordingly, some embodiments include substitutents attached to one or more conjugated macrocycles where the substituents serve to prevent aggregation of the molecules in the bulk phase. Conjugated macrocycle substituents can include H, electron-donating groups, and/or electron-withdrawing groups in any number and combination. More particularly, conjugated macrocycle substituents can include one or more H, alkyl groups having 1 to about 20 carbon atoms, alkenyl groups having 2 to about 20 carbon atoms, alkynyl groups having 2 to about 20 carbon atoms, aryl groups having 3 to about 50 carbon atoms, arylalkynyl groups having 8 to about 24 carbon atoms,unsaturated heterocyclo having 4 to about 24 carbon atoms, heteroaryl having 2 to about 50 carbon atoms, unsaturated heterocycloalkenyl, unsaturated heterocycloalkynyl or heteroarylalkynyl, and groups including, but not limited to, halo, amino, nitro, nitroso, cyano, azido, aldehyde, carboxyl, carbonyl, alkylcarbonyl, alkoxycarbonyl, aminocarbonyl, alkoxy, hydroxyl, mercapto, thiolato, sulfo, phosphino, phospho, and phosphono, to name a few.

The compounds of Formula I can comprise one or more conjugated macrocycles. For instance, the compounds can comprise from about 1 to about 50, about 1 to about 25, about 1 to about 10, about 1 to about 5, or about 2 conjugated macrocycles. In embodiments in which a plurality of conjugated macrocyles are present, the conjugated macrocycles are preferably linked either directly or through linking group $R_M$. This linking group can encompass virtually any covalent linkage known in the art, including simple covalent bonds, alkyl having 1 to about 20 carbon atoms, alkenyl having 2 to about 20 carbon atoms, cumulenyl having 4 to about 14 carbon atoms, alkynyl having 2 to about 20 carbon atoms, aryl having 3 to about 50 carbon atoms, arylalkynyl having 8 to about 24 carbon atoms, arylalkenyl having 8 to about 24 carbon atoms, unsaturated heterocyclo having 4 to about 24 carbon atoms, heteroaryl having 2 to about 50 carbon atoms, unsaturated heterocycloalkenyl, unsaturated heterocycloalkynyl or heteroarylalkynyl. These linking groups can be attached to any site of the conjugated macrocycles. For example, when the conjugated macrocycle is a porphyrin, linking groups can be attached to either the meso or pyrrolic (β) positions.

The $R_1$ and $R_2$ terminal groups of the present compounds are each attached to the conjugated macrocycles through a linker moiety, $R_A$, which serves not only to connect electron donor and acceptor groups to the bridging macrocycle, but also to mediate electronic coupling. This linker moiety can include a covalent bond, alkenyl groups having 2 to about 20 carbon atoms, cumulenyl groups having 4 to about 14 carbon atoms, alkynyl groups having 2 to about 20 carbon atoms, aryl groups having 3 to about 50 carbon atoms, arylalkynyl groups having 8 to about 24 carbon atoms, unsaturated heterocyclo having 4 to about 24 carbon atoms, heteroaryl having 2 to about 50 carbon atoms, unsaturated heterocycloalkenyl, unsaturated heterocycloalkynyl or heteroarylalkynyl. Linker moiety $R_A$ can be attached to any position on the conjugated macrocyle. For example, when the conjugate macrocycle is a porphyrin, $R_A$ can be attached to meso or pyrrolic (β) positions. In some embodiments, the two $R_A$ groups are attached at opposite meso positions in a porphyrin (i.e., at the 5 and 15 positions or the 10 and 20 positions on the porphyrin ring).

The terminal groups of the present compounds are represented by $R_1$ and $R_2$. $R_1$ can include H, halo, a protecting group, an organic electron donor group or an inorganic electron donor moiety. $R_2$ can include H, halo, a protecting group, an organic electron acceptor group or an inorganic electron acceptor moiety. At least one of $R_1$ and $R_2$ is an inorganic moiety, and in further embodiments, $R_1$ and $R_2$ are both inorganic moieties. The present invention also includes embodiments in which one of $R_1$ and $R_2$ is an inorganic moiety and the other is an organic electron donor or electron acceptor group.

An "inorganic moiety," as used throughout, refers to a chemical group comprising at least one metal atom or metalloid atom (semimetal such as, e.g., B, Si, As, or Te). The inorganic moiety can include main group elements and/or main group clusters such as for example, carboranes. According to some embodiments, the metal or metalloid atoms of an inorganic moiety can be bonded or complexed with at least one organic ligand. Inorganic moieties can include metal complexes (a metal atom complexed with an organic ligand) or metalloid complexes (a metalloid atom complexed with an organic ligand). Organic ligands of inorganic moieties can include virtually any organic molecule that is capable of complexing with a metal or metalloid atom. In some embodiments, no organic ligand of an inorganic moiety is a conjugated macrocycle having more than 18 carbon atoms. In other embodiments, no organic ligand of an inorganic moiety comprises a conjugated macrocycle. In further embodiments, an organic ligand of an inorganic moiety is different than bridging moiety MC. For example, in embodiments where MC is a porphyrin, at least one inorganic moiety of the compound preferably comprises no porphyrin ligand.

In preferred embodiments of the present invention, one of $R_1$ and $R_2$ is an organic electron donor group or inorganic electron donor moiety and the other of $R_1$ and $R_2$ is an organic electron acceptor group or inorganic electron acceptor moiety. Donors and acceptors can be identified relative to each other. For example, in comparing two chemical moieties, the group that is more electron donating (or less electron accepting) can be considered as the electron donor group. Conversely, the group that is more electron accepting (or less electron donating) can be considered as the electron acceptor group. Electron donating or accepting ability can be readily determined by one skilled in the art by, for example, measuring and comparing inductive effects. Inductive effects, a measure of how much a substituent either donates or withdraws electron density from the core molecule to which it is attached, are well known to those skilled in the art and explained in substantial detail, for example, in March, *Advanced Organic Chemistry*, $3^{rd}$ ed., John Wiley & Sons, New York, 1985. Electron donors and acceptors can also be identified, for example, by measuring and comparing resting potentials. A group that is more easily oxidized (has a lower resting potential) than another can be considered an electron donor. Conversely, a group that is more easily reduced (has a higher resting potential) than another group can be considered an electron acceptor. Comparison of resting potentials can be convenient for comparing the electron donating or accepting ability of inorganic moieties, such as, for example, metal or metalloid complexes. Measurement of resting potential by various electrochemical techniques is well known to those skilled in the art.

Metal complexes of the present invention comprise at least one metal atom and at least one organic ligand. Any metal atom, in any of its accessible oxidation states, is suitable, including transition metals, lanthanides, actinides, alkaline earth, alkali metals, and main group metals. Transition metals include Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, and Hg. Main group metals include Al, Ga, Ge, In, Sn, Sb, Tl, Pb, Bi, and Po. In some embodiments, compounds of the present invention include Group 8 transition metals (including Fe, Ru, and Os). In other embodiments, compounds of the present invention include Rh and Pt. Metal complexes having relatively high thermal stability, such as those comprising second and third row transition metals, are also suitable.

Metal complexes can include any suitable ligand system and preferably include at least one organic ligand that can be covalently bound to the $R_A$ linking moiety. Suitable organic ligands of metal complexes can be monodentate, bidentate, multidentate, π-bonding, organic, inorganic, charged, or uncharged. Further, organic ligands preferably comprise one or more heteroatoms through which the metal atom is coordinated, although organometallic compounds comprising coordinating carbon are also suitable. Coordinating heteroatoms of the organic ligands can include oxygen, nitrogen, sulphur, phosphorus, boron, and p-block elements. Nitrogen-containing organic ligands can include amines, nitrenes, diazenes, triazenes, polypyrazolylborates, heterocycles such as 2,2'-bipyridine (bpy), 1,10-phenanthroline, terpyridine (trpy), pyridazine, pyrimidine, purine, pyrazine, pyridine, 1,8-napthyridine, pyrazolate, imidazolate, and macrocycles including those with and without a conjugated π system, and the like. Preferred nitrogen-containing organic ligands include those that comprise one or more heterocycles such as pyridine and polypyridyl ligands such as terpyridine (trpy), bipyridine (bpy), and derivatives thereof. Phosphorus-containing organic ligands typically include phosphines and related di- and trivalent phophorous compounds. Oxygen-containing organic ligands include alkoxides, alcohols, aryloxides, ethers, ketones, esters, carboxylates, crown ethers, β-diketones, carbamate, dimethylsulfoxide, and related groups. Sulfur-containing ligands can include thiols, thiolates, thioether, dithiocarbamates, 1,2-dithiolenes, and the like. Organic ligands comprising coordinating carbon atoms can include alkyl, alkenes, alkynes, and cyclopentadienide. Metal complexes can also comprise other ligands, including inorganic ligands such as halides, azide, nitric oxide, hydrogen sulfide, disulfides, sulfide, water, hydroxide, oxo, superoxide, peroxide, and oxo anions such as carbonate, nitrate, nitrite, sulfate, sulfite, phosphate, perchlorate, molybdate, tungstate, oxalate. Metal complexes containing these and other ligands are described in detail in Cotton and Wilkinson, *Advanced Inorganic Chemistry*, Fourth Ed., John Wiley & Sons, New York, 1980, which is incorporated herein by reference in its entirety.

Organic ligands can be further derivatized with one or more charged substituents, such as anionic or cationic groups, to fully or partially neutralize any positive or negative formal charge associated with the metal atoms of the metal complexes. Suitable anionic substituents can include carbonate, nitrate, nitrite, sulfate, sulfite, phosphate, polyoxometalates, sulfide, borate, triflate, carboxylate, phenolate, and the like. Preferred metal complexes are characterized by ligand to metal charge transfer (LMCT) transitions or metal to ligand charge transfer (MLCT) transitions. Such complexes include, inter alia, certain heteroaryl and/or polypyridyl complexes of transition metals such as bis(trpy) and tris(bpy) complexes. Particularly preferred complexes include bis(trpy) complexes of Group 8 transition metals such as $[Ru(II)(trpy)_2]^{2+}$, $[Ru(III)(trpy)_2]^{3+}$, $[OS(II)(trpy)_2]^{2+}$, $[OS(III)(trpy)_2]^{3+}$. These bis(trpy) complexes can be attached to the linking $R_A$ group through any atom of a terpyridyl ligand. In some embodiments $R_A$ is attached through the 4' position.

Metalloid complexes comprise at least one metalloid atom (e.g., B, Si, as, or Te) and at least one organic ligand to which the metalloid is bonded. Some metalloid complexes include organoboranes, carboranes, organosilanes, and the like.

Organic electron donor and organic electron acceptor groups can be any of a wide range of non-metal containing functional groups. In preferred embodiments, an organic electron donor comprises at least one electron-donating substituent. Conversely, an organic electron acceptor preferably comprises at least one electron-withdrawing substituent. Preferred electron donor groups include alkyl and aryl groups bearing at least one substituent that is electron-donating such as aryl substituted by dialkylamino or diarylamino (e.g., 4-dimethylaminophenyl and 4-diphenylaminophenyl). Other electron donor groups include organic moieties that are electron donating relative to hydrogen. Electron donating groups are easily recognized by one skilled in the art and can be determined by measuring inductive effects compared with hydrogen. For example, a group that donates more electron density onto the molecule to which it is attached relative to a hydrogen substituent is considered electron-donating. Representative electron donating groups include $NH_2$, alkoxy groups, OH, alkylthio groups, SH, —OC(O)-(alkyl), cycloheptatrienes, and heterocycles such as julolidinyl groups (See, e.g., Marder, et al., *Science,* 1994, 263, 511, which is incorporated herein by reference in its entirety). In a similar manner, preferred electron acceptor groups include alkyl and aryl groups bearing at least one substituent that is electron-withdrawing such as aryl substituted by nitro or cyano (e.g., 4-nitrophenyl and 4-cyanophenyl). Other electron acceptor groups include organic moieties that are electron withdrawing relative to hydrogen. Electron withdrawing groups are well recognized by one skilled in the art and can be determined by measuring inductive effects compared with hydrogen. For example, a group that withdraws more electron density from the molecule to which it is attached relative to a hydrogen substituent is electron-withdrawing. Representative electron acceptor groups include alkyl and aryl groups substituted by at least one electron withdrawing group (such as haloalkyl and haloaryl). Representative electron withdrawing groups include, inter alia, $N(alkyl)_3^+$, $S-(alkyl)_2^+$, $NH_3^+$, $NO_2$, $SO_2(alkyl)$, CN, $SO_2(aryl)$, COOH, halo, cyclopentadienyl, C(O)O-(alkyl), C(O)-(alkyl), CHO, pyridinium, and heterocycles such as N,N'-diethylthiobarbituric acid, 3-phenyl-5-isoxazolone, quinone, 4-pyridyl, and 3-pyridyl groups. Electron donor and acceptor groups are further described in U.S. Pat. No. 5,783,306, which is incorporated herein by reference in its entirety.

According to the present invention, $R_1$ or $R_2$ can also be a protecting group. Protecting groups render a chemical functionality of a molecule inert to specific reaction conditions and can later be removed from such functionality in a molecule without substantially damaging or altering the remainder of the molecule. For example, when $R_A$ comprises an ethynyl moiety, $R^1$ (and/or $R^2$) can be an ethynyl protecting group that, for instance, blocks reactivity of terminal ethynyl under certain reaction conditions and is selectively removed under another set of conditions. Preferred ethynyl protecting groups include triarylsilyl and trialkylsilyl groups such as trimethysilyl (TMS) or triisopropylsilyl (TIPS). Protecting groups and their chemistry are well known in the art and described, for example, in Greene, T. W., et al., *Protecting Groups in Organic Synthesis,* $2^{nd}$ edition, John Wiley and Sons, Inc., New York, (1991), which is incorporated herein by reference in its entirety.

The compounds of the present invention can be capable of undergoing multiple redox events and therefore can be stable in a wide range of oxidation states. Accordingly, any of Formulas I-V can be charged or uncharged. Charge can be positive or negative. Positively charged compounds can have a charge (n) of 1, 2, 3, 4, 5, 6, 7, 8, 9, 10, 11, 12, or more, up to about 100, for example. Negatively charged compounds can have a charge (n) of −1, −2, −3, −4, −5, −6, −7, −8, −9, −10, −11, −12, or lower, down to about −100, for example. In embodiments, n can be about −2 to about 2, about −4 to about 4, about −8 to about 8, or about −12 to about 12. In some embodiments, the present compounds are uncharged (n=0). Charged compounds of the present invention can be isolated as salts comprising one or more counter ions (X). As an example, for any compound of charge n, counter ions in an isolated salt of the compound can be represented by $(n/|r|)X^r$, where r is the charge of X and $n/|r|$ represents the number of counter ions. Any counter ion or combination of counter ions is suitable. Some typical weakly or non-coordinating counter anions include, for example, $BF_4^-$, $BPh_4^-$, $PF_6^-$, $SbF_6^-$, $ClO_4^-$, triflate, and the like. Counter cations can include, for example, ammonium ions, phosphonium ions, and the like. Such cations include, for example, $NH_4^+$, $N(Me)_4^+$, $N(Et)_4^+$, $P(Ph)_4^+$, and others.

As referred to throughout the present disclosure, alkyl groups are aliphatic and substituted aliphatic groups having from 1 to about 10 carbon atoms, including methyl, ethyl, and tert-butyl groups. Aryl groups are aromatic and substituted aromatic groups having 3 to about 50 carbon atoms (preferably 6 to about 50 carbon atoms), including phenyl, benzyl, pyridyl, and imidazolyl groups. Substituted aromatic groups can include, for example, 2,6-substituted phenyl where the substituents can include tert-butoxy or 3,3-dimethylbutoxy, for example. Cumulenyl groups are those having adjacent (or cumulative) carbon-carbon double bonds, preferably those having 4 to about 14 carbon atoms. Alkenyl can have 2 to about 20 carbon atoms and one or more carbon-carbon double bond, including ethenyl and butadienyl groups. Alkynyl groups can have 2 to about 20 carbon atoms and one or more carbon-carbon triple bonds, including ethynyl and butadiynyl groups. Arylalkynyl groups can have about 8 to about 24 carbon atoms and covalently bound aryl and alkynyl portions, such as diethynylbenzene groups. Heterocycloalkyl groups are cyclic alkyl groups having 4 to about 24 carbon atoms and oligomers thereof and comprise at least one heteroatom within the ring structure. Heterocyclo groups can comprise multiple unsaturations. Heteroaryl groups are aromatic groups having 2 to about 50 carbon atoms and at least one heteroatom within the aromatic ring system. Some representative heteroaryl groups can include, for example, pyridine, thiophene, furan, oligomers thereof, and the like, as well as porphyrin. Heterocycloalkynyl groups have covalently bound heterocycloalkyl and alkynyl portions. Heterocycloalkenyl groups have covalently bound heterocyclo and alkenyl portions. Heteroarylalkynyl groups have covalently bound heteroaryl and alkynyl portions. Heteroarylalkenyl groups covalently bound heteroaryl and alkenyl portions. Any of the above mentioned groups can be substituted or unsubstituted. Substituents can include, for example, H, electron-withdrawing groups, or electron-donating groups.

Electron-withdrawing groups are substituents that tend to draw electron density away from the compound to which it is attached. Examples of electron-withdrawing groups include halo, nitro, cyano, carboxyl, carboxylic esters, sulfoxides, sulfones, sulfonamides, ketones, aldehydes, and certain metal complexes. Electron-withdrawing groups are well recognized by those skilled in the art and can be identified by routine methods such as by measuring and comparing inductive effects relative to a hydrogen substituent. Electron-donating groups are substituents that tend to push electron density toward from the compound to which it is attached. Examples of electron-donating groups include peroxo, hydroxy, alkoxy, esters, alkyl, amino, amido, thiol, thiolates, certain metal complexes, and the like. Electron-donating groups are well recognized by those skilled in the art and can be identified by routine methods such as by measuring and comparing of inductive effects relative to a hydrogen substituent.

In other embodiments, the compounds of the present invention have Formula II or III

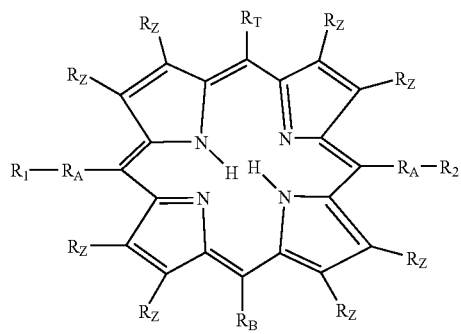

II

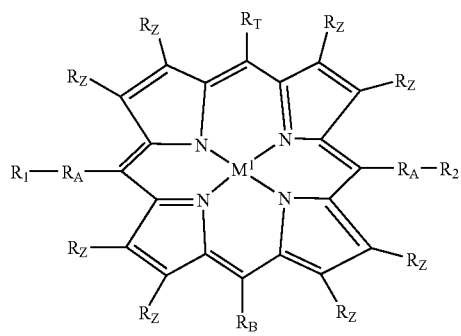

III wherein $M^1$ is a metal atom such as a transition metal, main group metal, lanthanide, actinide, alkaline earth, or alkali metal. Each $R_A$ is, independently, a covalent bond, alkenyl having 2 to about 20 carbon atoms, cumulenyl having 4 to about 14 carbon atoms, or alkynyl having 2 to about 20 carbon atoms; $R^1$ is H, halo, a protecting group, an organic electron donor group, or an inorganic electron donor moiety; and $R_2$ is H, halo, a protecting group, an organic electron acceptor group or an inorganic electron acceptor moiety, wherein at least one of $R_1$ and $R_2$ is an inorganic moiety. According to some embodiments, the at least one inorganic moiety comprises at least one organic ligand other than a porphyrin. Each $R_T$ and $R_B$ is, independently, alkyl having 1 to about 20 carbon atoms, alkenyl having 2 to about 20 carbon atoms; alkynyl having 2 to about 20 carbon atoms, aryl having 3 to about 50 carbon atoms, arylalkynyl having 8 to about 24 carbon atoms, heteroaryl having 2 to about 50 carbon atoms, unsaturated heterocyclo having 4 to about 24 carbon atoms, unsaturated heterocycloalkenyl, or unsaturated heterocycloalkynyl, wherein each $R_T$ and $R_B$ is optionally further substituted by one or more substituents; and each $R_Z$ is, independently, H, an electron-donating group, or an electron-withdrawing group. Compounds of Formulas II and III can be charged or uncharged.

In certain embodiments according to Formulas II and III, $M^1$ is a transition metal such as Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, or Hg. In other embodiments, $M^1$ is a main group metal. Preferred organic electron donor groups include dialkylaminoaryl such as 4-dimethylaminophenyl and diarylaminoaryl such as 4-diphenylaminophenyl. Some preferred organic electron acceptor groups include N,N'-diethylthiobarbituric acid, 3-phenyl-5-isoxazolone, quinone, 4-pyridyl, 3-pyridyl, and nitroaryl such as, for example, 4-nitrophenyl. $R_T$, $R_B$, and $R_Z$ can comprise sterically bulky groups chosen or designed to influence molecular order in the bulk phase. For example, these groups can be selected to reduce or prevent aggregation of the molecules in the bulk phase. Particularly preferred $R_T$ and $R_B$ groups are 2,6-substituted phenyl where the substituents can comprise t-butoxy, 3,3-dimethylbutoxy, and the like. In other preferred embodiments, charge n is −12 to about 12. Compounds of Formula II and III also encompass those where both $R_1$ and $R_2$ are inorganic moieties.

In further embodiments, the compounds of the present invention have Formula IV or V

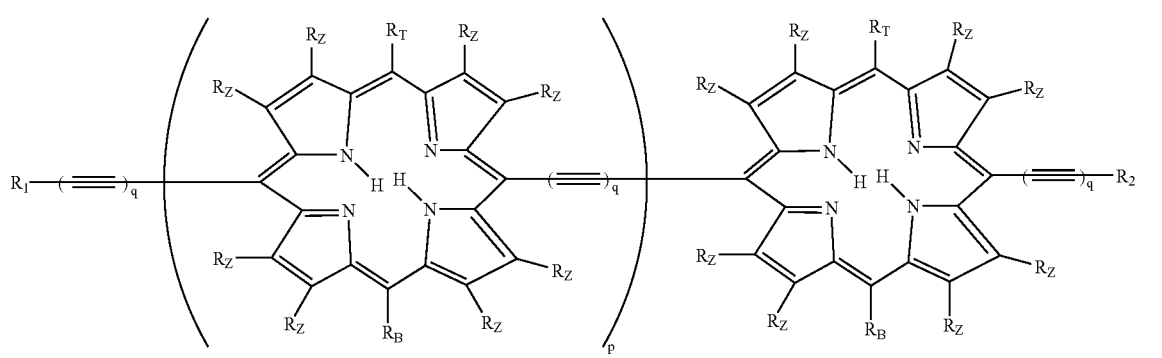

IV

-continued

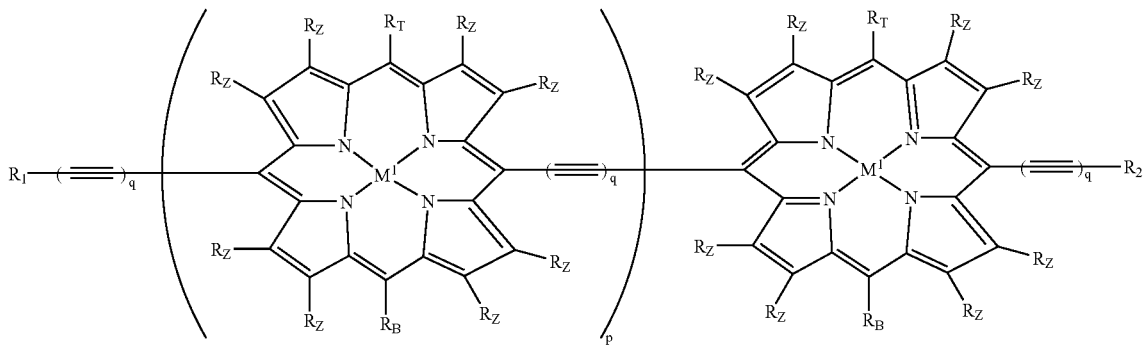

V wherein M¹ is a metal atom such as a transition metal, lanthanide, actinide, alkaline earth and alkali metal. $R_1$ is H, halo, a protecting group, an organic electron-donating group or an inorganic electron-donating moiety and $R_2$ is H, halo, a protecting group, an organic electron-accepting group or an inorganic electron-accepting moiety, provided at least one of $R_1$ and $R_2$ is an inorganic moiety. According to some embodiments, the at least one inorganic moiety comprises at least one organic ligand other than a porphyrin. Each $R_T$ and $R_B$ is, independently, alkyl having 1 to about 20 carbon atoms, alkenyl having 2 to about 20 carbon atoms; alkynyl having 2 to about 20 carbon atoms, aryl having 3 to about 50 carbon atoms, or arylalkynyl having 8 to about 24 carbon atoms, heteroaryl having 2 to about 50 carbon atoms, unsaturated heterocyclo having 4 to about 24 carbon atoms, unsaturated heterocycloalkynyl, or unsaturated heterocycloalkynyl wherein each $R_T$ and $R_B$ is optionally further substituted by one or more substituents; p is 0 to 50; and q is 1 to 5. Each $R_Z$ can be, independently, H, an electron-donating group, or an electron-withdrawing group. Compounds of formulas IV and V can be charged or uncharged.

In certain embodiments according to Formulas IV and V, M¹ is a transition metal such as Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, or Hg. In other embodiments, M¹ can be a main group metal. Preferred organic electron donor groups include dialkylaminoaryl such as 4-dimethylaminophenyl and diarylaminoaryl such as 4-diphenylaminophenyl. Preferred organic electron-accepting groups include N,N'-diethylthiobarbituric acid, 3-phenyl-5-isoxazolone, quinone, 4-pyridyl, 3-pyridyl, and nitroaryl such as, for example, 4-nitrophenyl. $R_T$, $R_B$, and $R_Z$ can comprise sterically bulky groups chosen or designed to influence molecular order in the bulk phase. For example, these groups can be selected to reduce or prevent aggregation of the molecules in the bulk phase. Particularly preferred $R_T$ and $R_B$ groups are 2,6-substituted phenyl where the substituents can comprise t-butoxy, 3,3-dimethylbutoxy, and the like. In other preferred embodiments, charge n is about −12 to about 12, and q is 1 or 2. Compounds of Formula IV and V also encompass those where both $R_1$ and $R_2$ are inorganic moieties.

Some embodiments of the present invention, such as compounds of Formulas II-V and certain compounds of Formula I, comprise a porphyrinato bridging moiety substituted by groups $R_A$-$R_1$ and $R_A$-$R_2$. Porphyrins are derivatives of porphine, a conjugated cyclic structure of four pyrrole rings linked through their 2- and 5-positions by methine bridges. Porphyrins can bear up to twelve substituents at meso and pyrrolic (beta) positions thereof. (See, e.g., U.S. Pat. No. 5,371,199, which is incorporated herein by reference in its entirety). Related heteroatom-containing compounds such as chlorins, phorbins, benzoporphyrins, bacteriochlorins, porphyrinogens, sapphyrins, texaphyrins, phthalocyanines, and their N-confused versions are also known. The chemistry of porphyrins, related macrocycles, and their metallated versions are well studied and described in a number of articles and treatises including Dolphin, ed., *The Porphyrins*, New York, Academic Press, 1978; Sessler, et al., *J. Am. Chem. Soc.*, 1988, 110, 5586; Sessler, et al., *Tetrahedron*, 1992, 48, 9661; Sessler, et al., *J. Org. Chem.* 1995, 60, 5975; Sessler, et al., *J. Am. Chem. Soc.* 1990, 112, 2810; Zollinger, *Color Chemistry*, New York, VCH Publishers, 1991; Okawara, et al., *Organic Colorants*, New York, Elsevier, 1988, and Kaeda, *Laser Dyes*, New York, Academic Press, 1984.

The compounds of the present invention can be prepared by a variety of methods, including for example, metal-mediated cross-coupling techniques. Metal-mediated cross-coupling is known to those skilled in the art as an efficient synthetic method for elaborating porphyrins and other related macrocycles as described in U.S. Pat. Nos. 5,371,199; 5,756, 723; 5,986,090; and 5,493,017 as well as International Patent Application Publication WO 94/04614; and other publications including, DiMagno, et al., *J. Am. Chem. Soc.* 1993, 115, 2513; DiMagno, et al., *J. Org. Chem.* 1993, 58, 5983; and Lin, et al., *Science,* 1994, 264, 1105, each of which is incorporated herein by reference in its entirety. Condensation techniques are also useful in the preparation of the present compounds and are described, for example, in DiMagno, et al., *J. Org. Chem.* 1994, 59, 6943.

Generally, the present compounds can be assembled by covalently coupling appropriately derivatized starting materials using metal-mediated cross-coupling techniques. A general process for preparing compounds of the present invention involves contacting a conjugated macrocycle precursor, such as a porphyrin-containing precursor with an inorganic moiety precursor. The conjugated macrocycle precursor comprises a conjugated macrocycle bearing a first reactive substituent. The inorganic moiety precursor comprises an inorganic moiety bearing a second reactive substituent. In some embodiments, the second reactive substituent is attached to an organic ligand of the inorganic moiety precursor. Contacting can be carried out in the presence of one or more metal-containing catalysts under metal-mediated cross-coupling reaction conditions for a time and at a temperature sufficient to form a covalent linkage between the conjugated macrocycle and inorganic moiety precursor. Preferably, one of either the first or second reactive substituents is an organic group such as alkyl having 1 to about 20 carbon atoms, alkenyl having 2 to about 20 carbon atoms, or alkynyl having 2 to about 20 carbon atoms, aryl having 3 to about 50 carbon atoms, or arylalkynyl having 8 to about 24 carbon atoms, arylalkenyl having 8 to about 24 carbon atoms, unsaturated heterocyclo having 4 to about 24 carbon atoms, heteroaryl having 2 to about 50 carbon atoms, unsaturated heterocycloalkenyl, unsaturated heterocycloalkynyl or heterocycloalkynyl; and the other of the reactive substituents is a leaving group such as chloro, fluoro, bromo, iodo, p-(2,4-dinitroanilino)benzenesulfonyl, benzenesulfonyl, methylsulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazolesulfonyl, and 2,4,6-trichlorophenyl.

Appropriate catalysts and mechanisms for metal-mediated cross-coupling reactions are described in detail in U.S. Pat. No. 5,756,723, which is incorporated herein by reference in its entirety. The principles and techniques relating to metal-mediated cross coupling are well known to those skilled in the art to consist of three general steps: (1) oxidative addition, (2) transmetalation, and (3) reductive elimination. See, e.g., Collman, et al., *Principles and Applications of Organotransition Metal Chemistry*, University Science Books, 1987, Mill Valley, Calif.; Kumada, *Pure & Appl. Chem.*, 1980, 52, 669; Hayashi, et al., *Tetrahedron Letters*, 1979, 21, 1871, each of which is incorporated herein by reference in its entirety.

Starting materials bearing a plurality of potentially reactive substituents can also comprise protecting groups to prevent unwanted side reactions or low yields. In embodiments where starting materials bear alkynyl groups such as ethynyl, preferred protecting groups include trialkylsilyl moieties. Methods for addition and removal of alkynyl protecting groups are well known to those skilled in the art.

Starting materials comprising metal complexes are readily prepared by routine methods. Suitable metal complexes can be made, for instance, by ligand exchange reactions. Ligands bearing desirable substituents such as halo can be prepared by standard organic chemistry reactions available in the literature. Coupled products of the above-described metal-mediated cross-coupling reactions can be monitored or identified by means well known to those skilled in the art. For example, $H^1$ NMR and mass spectrometry, and standard types of chromatographic analyses can be appropriate for monitoring reaction progress and identifying products and intermediates. Isolation of the present compounds can be achieved by any suitable means including chromatography and/or crystallization.

The compounds of the present invention can be used in the preparation of nonlinear optical devices. Devices, according to the present invention, comprise a substrate and a layer disposed on the substrate. Suitable substrates include metals, semiconductors such as silicon or gallium arsenide, and insulators such as ceramic, glass, or plastic. The substrate can be rigid or flexible. An example of a flexible substrate is Mylar®. The layer comprises at least one compound of the present invention, optionally in polymeric form, and is preferably a thin film. Thin films normally have a thickness of less than ten microns but can range from one molecule thick, about 10 Å, up to about 1000 Å. Preferably the film is non-centrosymmetric as a result of, for instance, electric-field or corona poling, Langmuir-Blodgett techniques, or alternating polyelectrolyte deposition.

In some embodiments, the layer can contain a compound of the present invention in combination with one or more synthetic organic polymers. The resulting polymeric composition can be polarizable or hyperpolarizable. In some embodiments, for example, the layer can include synthetic organic polymers or precursors thereof (e.g., monomers, catalysts, and sensitizers) in admixture with a compound of the invention. Such embodiments offer the possibility of effecting cross-linking and/or in situ polymerization following mixture of the polymer or polymer precursor system with a compound of the invention. According to some embodiments, the polymer constitutes a major proportion of the layer and the compound constitutes a minor proportion of the layer. Representative synthetic organic polymers include polyimides, polyacrylates, polymethacrylates, polyesters, polycarbonates, polystyrenes, polyolefins, polyvinyl ethers, polyquinolines, polyurethanes, and fluorocarbon-based polymers. Polyimides and other transparent polymers having high $T_g$ are preferred. A wide variety of polymeric compositions comprising polymer and compounds of the present invention can be prepared such as described in U.S. Pat. Nos. 5,371,199 and 5,783,306, each of which is incorporated herein by reference in its entirety.

According to some embodiments, compounds of the invention include functional groups that improve the compound's solubility in a polymer or precursor of interest. Compounds of the present invention can also be covalently bound with a wide variety of polymers, through use of linking moieties such as alkyl, alkoxyl, ester, amide, cyano, ether, and alkylamino groups.

The coating of a substrate with a material comprising a compound of the invention can be accomplished by any means known in the art, preferably by spin-coating, roll-coating, or physical vapor deposition. L. I. Maissel and R. Glang, *Handbook of Thin Film Technology*, McGraw-Hill (1970); Satas, *Coating Technology Handbook*, Marcel Dekker (1991). The materials used to form the layer can further include other moieties such as, for example, pigments, dyes, filters and dopants.

Polymerization and/or crosslinking of a layer following its deposition on a substrate can be accomplished in any of the ways known to those skilled in the art. For example, certain polymerizations can be effected by simple heating in the presence of a suitable initiator or by the incidence of light or some other form of electromagnetic energy in the presence or absence of a sensitizer. The latter procedure is preferred due to the ability of those in the art to effect selective, patterned polymerization through the use of, for example, removable masking agents. As will be recognized, devices incorporating appropriately arrayed patterns of polymer can be employed in microcircuitry and other applications.

In further embodiments, certain devices of the invention comprise a conductor superstrate disposed on the layer, a control means, and contacts attached to substrate and superstrate as described in, for example, U.S. Pat. No. 5,783,306, incorporated herein by reference in its entirety. This arrangement allows an input light signal from a source to be operated upon by virtue of a changing electric field within the layer generated by the control means in concert with the contacts. An altered or "operated" light signal is directed away from the layer to a suitable detector. A wide variety of devices fitting this general description are well-known to those skilled in the art. Representative examples are disclosed by Burland, et al., *Chem. Rev.* 1994, 94, 31. Compounds of the present invention can also be used as components of photovoltaic cells, optical fibers, optical amplifiers, lasers, molecular devices, light emitting devices, and integrated electronic devices. Some representative devices include electro-optic modulators (including high speed electro-optic modulators for signal processing at optical wavelengths), wave guides, phase shifters, optical limiting devices (including optical limiting devices for optical telecommunication wavelengths, such as near-infrared wavelengths), signal processors, frequency boosting devices, holographic data storage devices, and the like. These, and other devices, are well known in the art and some examples of their structure and manufacture are provided in, for example, U.S. Pat. Nos. 5,741,442; 6,067,186; and 6,348,992, each of which is incorporated by reference in its entirety.

According to some embodiments, compositions comprising polymer and compounds of the present invention can be photorefractive. The basic elements of photorefractivity include photosensitivity, photoconductivity, and electro-optic acitivity, which, collectively, can allow the recording of optical information, such as holographic data, through the formation of refractive index variations in the composition. It is believed that two intersecting laser beams create an interference pattern (optical intensity pattern) that, when directed to a photorefractive material, generates an internal electric field that, in turn, changes the refractive index of the material. This results in the recording of the optical intensity pattern in the form of a refractive index pattern. Such materials have potential use in photodynamic therapy as well as biological and non-biological imaging applications. Devices comprising photorefractive materials and use of such devices in storing holographic data and biological imaging are well known in the art and described, for example, in U.S. Pat. Nos. 5,064,264 and 6,090,332, each of which is incorporated herein by reference in its entirety.

According to some embodiments, devices comprising compounds of the present invention can be hermetically sealed to improve photochemical stability. Devices can be protected from air by any means known in the art, such as by hermetically packaging the device in a container filled with an inert gas. In another example, the device can be coated with a polymeric material that has low permeativity to oxygen. These and other methods for hermetically sealing devices are described, for example, in U.S. Pat. No. 6,348,992, which is incorporated herein by reference in its entirety.

Advantages of the present compounds are numerous and readily apparent to those skilled in the art. In particular, incorporation of metal complexes as electron donor and/or accepting groups provides enhanced thermal stability, allowing for a wider range of optoelectronic applications. The present compounds allow one to take advantage of collective oscillator photophysics in the engineering of NLO chromophores, and incorporate numerous parameters to facilitate tailoring of photophysical properties.

EXAMPLES

The following examples describe synthetic preparations of compounds of the present invention and intermediates thereof. All manipulations were carried out under nitrogen previously passed through an $O_2$ scrubbing tower (Schweizerhall R3-11 catalyst) and a drying tower (Linde 3-Å molecular sieves) unless otherwise stated. Air-sensitive solids were handled in a Braun 150-M glove box. Standard Schlenk techniques were employed to manipulate air-sensitive solutions. All solvents utilized in this work were obtained from Fisher Scientific (HPLC Grade). Tetrahydrofuran (THF) was distilled from Na/benzophenone under $N_2$. Diethylamine and triethylamine were dried over KOH pellets and distilled under vacuum. All NMR solvents were used as received. Reagents 3,3-dimethyl-1-butanol, resorcinol, diethylazodicarboxylate (DEAD), triphenylphosphine ($PPh_3$), n-butyllithium, boron trifluoride etherate ($BF_3.OEt_2$), tetramethylethylenediamine (TMEDA), 1,2-dichloro-4,5-dicyano-benzoquinone (DDQ), 2,6-bis-pyridyl-4-(1H)-pyridone, phosphorus pentabromide ($PBr_5$), phosphorus oxybromide ($POBr_3$), potassium carbonate ($K_2CO_3$), potassium nitrate ($KNO_3$), potassium fluoride, N-ethyl-morpholine, ammonium hexafluorophosphate ($NH_4PF_6$), sodium borohydride, trifluoroacetic acid, N-bromosuccinimide (NBS), zinc(II) acetate, TBAF (1 M in THF), methyl-lithium (lithium bromide complex, 1.5 M, hexanes), 2,2';6',2"-terpyridine (tpy), $RuCl_3$, $Na_2OsCl_6$, trimethylsilylacetylene, triisopropylsilylacetylene, $ZnCl_2$ $Pd_2dba_3$, $AsPh_3$, $Pd(PPh_3)_4$ and copper(I)iodide, were used as received (Aldrich or Strem). 2,2'-Dipyrrylmethane, trimethylsilylethynyl zinc chloride, 4'-bromo-(2,2';6',2"-terpyridine) (Br-tpy) and Ru(tpy)Cl$_3$ were prepared by literature methods. Chemical shifts for $^1$H-NMR spectra are relative to the solvent residual protium ($CDCl_3$, δ=7.24 ppm; acetonitrile-$d_3$, δ=1.93 ppm; pyridine-$d_5$, δ=8.74 ppm). All J values are reported in Hertz. The number of attached protons is found in parentheses following the chemical shift value. Chromatographic purification (silica gel 60, 230-400 mesh, EM Scientific) of all newly synthesized compounds was accomplished on the bench top. High resolution mass spectroscopic analyses were performed at the University of Pennsylvania Mass Spectrometry Center. Standard abbreviations for metal polypyridyl compounds and terpyridyl are used throughout the experimental section.

Electronic spectra were recorded on an OLIS UV/Vis/NIR spectrophotometry system that is based on the optics of a Cary 14 spectrophotometer. NMR spectra were recorded on a 250-MHz AC-250 Bruker spectrometer. Cyclic voltammetric measurements were carried out with an EG&G Princeton Applied Research Model 273A Potentiostat/Galvanostat equipped with a single-compartment electrochemical cell.

Example 1

Ruthenium(II) 5-[4'-Ethynyl-(2,2';6',2"-terpyridinyl)]bis[10,20-di(2',6'-bis(3,3-dimethylbutoxy)phenyl)porphinato]zinc(II)-(2,2';6',2"-terpyridine)$^{2+}$bis-hexafluorophosphate [Ru(tpy)$_2$-C≡C—PZn] (1)

[5-Ethynyl-10,20-di(2',6'-bis(3,3-dimethylbutoxy)phenyl)porphinato]zinc(II) (193 mg, 0.20 mmol), [Ru(tpy)(4'-Br-tpy)](PF$_6$)$_2$ (200 mg, 0.21 mmol), diethylamine (8 mL), THF (30 mL) and acetonitrile (30 mL) were brought together in an oven-dried 100 mL Schlenk tube. The solution was degassed via three freeze-pump-thaw cycles following which Pd(PPh$_3$)$_4$ (50 mg, 0.04 mmol) and CuI (10 mg, 0.05 mmol) were added. The reaction was stirred under $N_2$ at 50° C. for 24 h, cooled to room temperature, and evaporated. The product was purified by column chromatography on silica using 80:17:3 acetonitrile:water:saturated $KNO_3$ as the eluant. The product eluted as a brownish green band; the volume of the product fraction was reduced to 50 mL, and ammonium hexafluorophosphate (1 g) in 10 mL of water was added, producing a brown precipitate. The product was filtered, washed successively with water and ether, and dried to give 250 mg of compound 1 as the hexafluorophosphate salt (68% yield, based on 193 mg of the [5-ethynyl-10,20-di(2',6'-bis(3,3-dimethylbutoxy)phenyl)porphinato]zinc(II) starting material). $^1$H-NMR (250 MHz, CD$_3$CN): 10.15 (s, 1 H), 9.99 (d, 2 H, J=4.7 Hz), 9.36 (s, 2 H), 9.28 (d, 2 H, J=4.5 Hz), 9.00 (d, 2 H, J=4.6 Hz), 8.82 (d, 2 H, J=4.5 Hz), 8.78 (d, 4 H, J=8.2 Hz), 8.52 (d, 2 H, J=8.0 Hz), 8.45 (t, 1 H, J=8.5 Hz), 7.97 (t, 2 H, J=8.2 Hz), 7.94 (t, 2 H, J=8.2 Hz), 7.81 (t, 2 H, J=8.4 Hz), 7.56 (d, 2 H, J=5.3 Hz), 7.41 (d, 2 H, J=5.3 Hz), 7.2 (m, 4 H), 7.17 (d, 4 H, J=8.5 Hz), 3.98 (t, 8 H, J=7.1 Hz), 0.76 (t, 8 H, J=7.0 Hz), 0.19 (s, 36 H). LRMS (ESI$^+$) m/z: 1659.4 (calcd for $C_{88}H_{88}N_{10}O_4Ru_1ZnP_2F_{12}$ (M-PF$_6$)$^+$ 1659.5). m/z: 757.3 (calcd for $C_{88}H_{88}N_{10}O_4Ru_1Zn$ (M-2PF$_6$)$^{2+}$ 758.8).

Example 2

Osmium(II) 5-[4'-Ethynyl-(2,2';6',2"-terpyridinyl)] bis[10,20-di(2',6'-bis(3,3-dimethylbutoxy)phenyl) porphinato]zinc(II)-(2,2';6',2"-terpyridine)$^{2+}$bis-hexafluorophosphate [Os(tpy)$_2$-C≡C—PZn] (2)

[5-Ethynyl-10,20-di(2',6'-bis(3,3dimethylbutoxy)phenyl) porphinato]zinc(II) (192 mg, 0.20 mmol), [Os(tpy)(4'-Br-tpy)](PF$_6$)$_2$ (156 mg, 0.21 mmol), diethylamine (6 mL), THF (30 mL) and acetonitrile (30 mL) were brought together in an oven-dried 100 mL Schlenk tube. The solution was degassed via three freeze-pump-thaw cycles following which Pd(PPh$_3$)$_4$ (50 mg, 0.04 mmol) and CuI (10 mg, 0.05 mmol) were added. The reaction was stirred under N$_2$ at 50° C. for 24 h, cooled to room temperature, and evaporated. The product was purified by column chromatography on silica using 80:17:3 acetonitrile:water:saturated KNO$_3$ as the eluant. The product eluted as a brownish green band; the volum of the product fraction was reduced to 50 mL and ammonium hexafluorophosphate (1 g) in 10 mL of water was added, producing a brown precipitate. The product was filtered, washed successively with water and ether, and dried to give 80 mg of compound 2 as the hexafluorophosphate salt (21% yield based on 192 mg of the [5-ethynyl-10,20-di(2',6'-bis(3,3-dimethylbutoxy)phenyl)porphinato]zinc(II) starting material). $^1$H-NMR (250 MHz, CD$_3$CN): 10.11 (s, 1 H), 10.00 (d, 2 H, J=4.6 Hz), 9.38 (s, 2 H), 9.27 (d, 2 H, J=4.4 Hz), 8.99 (d, 2 H, J=4.6 Hz), 8.81 (d, 2 H, J=4.3 Hz), 8.75 (m, 4 H), 8.48 (d, 2 H, J=8.1 Hz), 7.97 (t, 1 H, J=8.2 Hz), 7.84 (m, 4 H), 7.78 (t, 2 H, J=8.4 Hz), 7.75 (m, 4 H), 7.41 (d, 2 H, J=5.6 Hz), 7.29 (d, 2 H, J=5.1 Hz), 7.17 (d, 4 H, J=8.5 Hz), 7.12 (4 H, m), 3.99 (t, 8 H, J=7.1 Hz), 0.78 (t, 8 H, J=7.1 Hz), 0.18 (s, 36 H). LRMS (ESI$^+$) m/z: 1604.4 (calcd for $C_{88}H_{88}N_{10}O_4OsZn$ (M-2PF$_6$)$^+$ 1603.6). m/z: 802.2 (calcd for $C_{88}H_{88}N_{10}O_4Ru_1Zn$ (M-2PF$_6$)$^{2+}$ 758.8).

Example 3

Bisruthenium(II) 5,15-Bis[4'-Ethynyl-(2,2';6',2"-terpyridinyl)]bis[10,20-di(2',6'-bis(3,3-dimethylbutoxy)phenyl)porphinato]zinc(II)-bis(2,2';6',2"-terpyridine)$^{4+}$tetrakis-hexafluorophosphate[Ru(tpy)$_2$-C≡C—PZn—C≡C—Ru(tpy)$_2$] (3)

[5,15-Bis(ethynyl)-10,20-di(2',6'-bis(3,3-dimethylbutoxy)phenyl)porphinato]zinc(II) (192 mg, 0.20 mmol), [Ru(tpy)(4'-Br-tpy)](PF$_6$)$_2$ (406 mg, 0.43 mmol), diethylamine (6 mL), THF (30 mL) and acetonitrile (30 mL) were brought together in an oven-dried 100 mL Schlenk tube. The solution was degassed via three freeze-pump-thaw cycles, following which Pd(PPh$_3$)$_4$ (50 mg, 0.04 mmol) and CuI (10 mg, 0.05 mmol) were added. The reaction was stirred under N$_2$ at 50° C. for 24 h, cooled to room temperature, and evaporated. The product was purified by column chromatography on silica using 80:17:3 acetonitrile:water:saturated KNO$_3$ as the eluant. Electronic absorption spectroscopy determined that the product eluted after several minor fractions as a brown band. The volume of the product fraction was reduced to 50 mL and ammonium hexafluorophosphate (1 g) in 10 mL of water was added, giving a brown precipitate. The product was filtered, washed successively with water and ether, and dried to give 220 mg of compound 3 as the hexafluorophosphate salt (42% yield based on 192 mg of the [5,15-bis(ethynyl)-10,20-di(2', 6'-bis(3,3-dimethylbutoxy)phenyl)porphinato]zinc(II) starting material). $^1$H-NMR (250 MHz, CD$_3$CN): 9.99 (d, 4 H, J=4.6 Hz), 9.39 (s, 4 H), 8.95 (d, 4 H, J=4.6 Hz), 8.80 (d, 8 H, J=8.2 Hz), 8.54 (d, 4 H, J=8.1 Hz), 8.46 (t, 2 H, J=8.1 Hz), 8.03 (t, 4 H, J=6.9 Hz), 7.95 (t, 4 H, J=7.8 Hz), 7.86 (t, 2 H, J=8.4 Hz), 7.57 (d, 4 H, J=5.5 Hz), 7.43 (d, 4 H, J=4.8 Hz), 7.25 (m, 8 H), 7.21 (d, 4 H, J=8.4 Hz), 4.04 (t, 8 H, J=6.9 Hz), 0.87 (t, 8 H, J=6.9 Hz), 0.21 (s, 36 H). LRMS (ESI$^+$) m/z: 1197.0 (calcd for $C_{120}H_{108}N_{16}O_4Ru_2ZnP_2F_{12}$ (M-2PF$_6$)$^{2+}$ 1197.3). m/z: 749.8 (calcd for $C_{120}H_{108}N_{16}O_4Ru_2ZnPF_6$ (M-3PF$_6$)$^{3+}$ 749.9).

Example 4

Bisosmium(II) 5,15-Bis[4'-Ethynyl-(2,2';6',2"-terpyridinyl)]bis[10,20-di(2',6'-bis(3,3-dimethylbutoxy)phenyl)porphinato]zinc(II)-bis(2,2';6',2"-terpyridine)$^{4+}$tetrakis-hexafluorophosphate [Os(tpy)$_2$-C≡C—PZn-C≡C—Os(tpy)$_2$] (4)

[5,15-Bis(ethynyl)-10,20-di(2',6'-bis(3,3-dimethylbutoxy)phenyl)porphinato]zinc(II) (250 mg, 0.256 mmol), [Os(tpy)(4'-Br-tpy)](PF$_6$)$_2$ (800 mg, 0.78 mmol), diisopropylamine (8 mL), THF (30 mL) and acetonitrile (30 mL) were brought together in an oven-dried 100 mL Schlenk tube. The solution was degassed via three freeze-pump-thaw cycles, following which Pd(PPh$_3$)$_4$ (30 mg, 0.026 mmol) and CuI (5 mg, 0.026 mmol) were added. The reaction was stirred under N$_2$ at 50° C. for 24 h, cooled to room temperature, and evaporated. The product was purified by column chromatography on silica using 80:17:3 acetonitrile:water:saturated KNO$_3$) as the eluant. Electronic absorption spectroscopy determined that the product eluted after several minor fractions as a brown band. The volume of the product fraction was reduced 50 mL and ammonium hexafluorophosphate (1 g) in 10 mL of water was added, yielding a brown precipitate. The product was filtered, washed successively with water and ether, and dried to give 670 mg of compound 4 as the hexafluorophosphate salt (91% yield based on 250 mg of the [5,15-bis(ethynyl)-10,20-di(2',6'-bis(3,3-dimethylbutoxy)phenyl)porphinato]zinc(II) starting material). $^1$H-NMR (250 MHz, CD$_3$CN): 9.97 (d, 4 H, J=4.5 Hz), 9.39 (s, 4 H), 8.94 (d, 4 H, J=4.5 Hz), 8.79 (t, 8 H, J=8.9 Hz), 8.51 (d, 4 H, J=7.1 Hz), 7.99 (t, 2 H, J=8.2 Hz), 7.84 (m, 10 H), 7.41 (d, 4 H, J=5.2 Hz), 7.32 (d, 4 H, J=5.1 Hz), 7.20 (m, 8 H), 4.04 (t, 8 H, J=6.9 Hz), 1.10 (t, 8 H, J=6.9 Hz), 0.20 (s, 36 H). LRMS (ESI$^+$) m/z: 2718.2 (calcd for $C_{120}H_{108}N_{16}O_4Os_2ZnP_3F_{18}$ (M-PF$_6$)$^+$ 2719.6). m/z: 1286.3 (calcd for $C_{120}H_{108}N_{16}O_4Os_2ZnP_2F_{12}$ (M-2PF$_6$)$^{2+}$ 1287.4). m/z: 1140.4 (calcd for $C_{120}H_{108}N_{16}O_4Os_2Zn$ (M-4PF$_6$)$^{2+}$ 1142.4).

Example 5

4'-Bromo-2,2';6',2"-terpyridine (5)

A 500 mL flask was charged with 2,6-bis-pyridyl-4-(1H)-pyridone (2.47 g, 9.9 mmol), phosphorus pentabromide (6.6 g, 15.4 mmol), and phosphorus oxybromide (30 g) and heated to 100° C. with stirring for 12 h, giving a black oily residue. The reaction was cooled to room temperature; ice was added cautiously to the reaction until the evolution of gas subsided. The reaction mixture was neutralized with K$_2$CO$_3$ (aq), extracted with CH$_2$Cl$_2$ (3×300 mL), dried over MgSO$_4$, and filtered. Removal of solvent gave a tan colored solid which was purified by column chromatography on neutral alumina using 2:1 CH$_2$Cl$_2$:hexanes as the eluant, providing 2.65 g of pure 4'-bromo-2,2';6',2"-terpyridine (86% yield, based on 2.47 g of the 2,6-bis-pyridyl-4-(1H)-pyridone starting material). $^1$H-NMR (250 MHz, CDCl$_3$): 8.68 (dq, 2 H, J=4.7 Hz, 0.8 Hz), 8.62 (s, 2 H), 8.56 (dt, 2 H, J=8.0 Hz, 1.0 Hz), 7.84 (td, J=7.7 Hz, 1.7 Hz), 7.33 (ddd, 2 H, J=7.6 Hz, 4.9 Hz, 1.2 Hz). HRMS (ESI$^+$) m/z: 333.9955 (calcd for C$_{15}$H$_{10}$N$_3$BrNa (M+Na)$^+$ 333.9956).

Example 6

[Ruthenium(II) (2,2';6',2"-Terpyridyl)(4'-bromo-2,2'; 6',2"-terpyridyl)](PF$_6$)$_2$ (6)

A 500 mL flask was charged with Ru(tpy)Cl$_3$ (2.20 g, 5 mmol), 4'-bromo-2,2';6',2"-terpyridine (1.62 g, 5.2 mmol), methanol (500 mL) and N-ethyl-morpholine (1 mL), refluxed for 2 h, and then cooled to room temperature. The solvent volume was reduced by 75%, following which it was diluted with an equal volume of aqueous ammonium hexafluorophosphate. The product precipitated as a red solid. This material was filtered, washed successively with water and ether, and dried to give 4.03 g of product (86% yield, based on 2.20 g of the Ru(tpy)Cl$_3$ starting material). $^1$H-NMR (250 MHz, CD$_3$CN): 8.97 (s, 2 H), 8.73 (d, 2 H, J=4.1 Hz), 8.47 (d, 4 H, J=8.0 Hz), 8.40 (t, 1 H, J=8.2 Hz), 7.91 (tq, 4 H, J=8.0 Hz, 1.7 Hz), 7.35 (m, 4 H), 7.16 (m, 4 H). HRMS (ESI$^+$) m/z: 790.9730 (calcd for C$_{30}$H$_{21}$N$_6$BrRuPF$_6$ (M-PF$_6$)$^+$ 790.9696).

Example 7

[Ruthenium(II) (2,2';6',2"-Terpyridyl)(4'-trimethylsilyl-ethynyl-2,2';6',2"-terpyridyl)](PF$_6$)$_2$ (7)

[Ru(tpy)(4'-Br-tpy)](PF$_6$)$_2$ (1.04 g, 1.11 mmol), trimethylsilylacetylene (3 mL, 22 mmol), diisopropylamine (8 mL), acetonitrile (50 mL), and THF (10 mL) were placed in an oven-dried 100 mL Schlenk tube. The solution was degassed via three freeze-pump-thaw cycles, following which Pd(PPh$_3$)$_4$ (250 mg, 0.22 mmol) and CuI (30 mg, 0.16 mmol) were added. The reaction was stirred under N$_2$ at 60° C. for 20 h, cooled to room temperature and evaporated to give a red residue. The material was purified by column chromatography on silica using 80:17:3 acetonitrile:water:saturated KNO$_3$ as the eluant. The product eluted as a dark red band; the volume of the product fractions was reduced to 50 mL and ammonium hexafluorophosphate (1 g) in 10 mL of water was added, yielding a red precipitate. The precipitate that formed following evaporation of the acetonitrile component of the solvent mixture was filtered, washed successively with water and ether, and dried, giving 930 mg of pure [Ru(tpy)(4'-trimethylsilyl-ethynyl)](PF$_6$)$_2$ (88% yield, based on 1.04 g of the [Ru(tpy)(4'-bromo-tpy)](PF$_6$)$_2$ starting material). $^1$H-NMR (250 MHz, CD$_3$CN): 8.76 (s, 2 H), 8.75 (d, 2 H, J=8.1 Hz), 8.49 (dd, 4 H, J=7.8 Hz, 3.2 Hz), 8.42 (t, 1 H, J=8.3 Hz), 7.91 (tq, 4 H, J=8.1 Hz, 1.6 Hz), 7.35 (d, 4 H, J=4.8 Hz), 7.14 (m, 4 H), 0.40 (s, 9 H). HRMS (ESI$^+$) m/z: 809.0980 (calcd for C$_{35}$H$_{30}$N$_6$SiRuPF$_6$ (M-PF$_6$)$^+$ 809.0987).

Example 8

[Ruthenium(II) (2,2';6',2"-Terpyridyl)(4'-ethynyl-2, 2';6',2"-terpyridyl)](PF$_6$)$_2$ (8)

[Ru(tpy)(4'-TMS-ethynyl)](PF$_6$)$_2$ (300 mg, 0.315 mmol) was dissolved in acetonitrile (50 mL). Potassium fluoride (500 mg, 8.6 mmol) was dissolved in a minimal amount of methanol and added to the acetonitrile solution. After stirring for 3 h, TLC analysis of the reaction mixture (80:17:3 acetonitrile:water:saturated KNO$_3$ showed complete formation of the product and consumption of the starting material. The product was purified by column chromatography on silica using acetonitrile:water:saturated KNO$_3$ (80:17:3) as the eluant. The product eluted as a dark red band; the volume of the product fraction was reduced to 50 mL and ammonium hexafluorophosphate (1 g) in 10 mL of water was added, yielding a red precipitate. The precipitate was filtered, washed successively with water and ether, and dried, giving 255 mg of product (92% based on 300 mg of the [Ru(tpy)(4'-trimethylsilyl-ethynyl)](PF$_6$)$_2$ starting material). $^1$H-NMR (250 MHz, CD$_3$CN): 8.82 (s, 2 H), 8.73 (d, 2 H, J=8.1 Hz), 8.48 (d, 4 H, J=8.2 Hz), 8.41 (t, 1 H, J=7.9 Hz), 7.92 (m, 4 H), 7.33 (d, 4 H, J=5.2 Hz), 7.15 (m, 4 H), 4.13 (s, 1 H). HRMS (ESI$^+$) m/z: 737.0625 (calcd for C$_{32}$H$_{22}$N$_6$RuPF$_6$ (M-PF$_6$)$^+$ 737.0591).

Example 9

[Osmium(II) (2,2';6',2"-Terpyridyl)(4'-bromo-2,2';6', 2"-terpyridyl)](PF$_6$)$_2$ (9)

Os(tpy)Cl$_3$ (1.06 g, 2.0 mmol) and 4'-bromo-2,2';6',2"-terpyridine (655 mg, 2.1 mmol) were refluxed in ethylene glycol (50 mL) for 1 h. The reaction mixture was cooled to room temperature and diluted with 50 mL of water. The solid precipitate was filtered, washed successively with water and ether, and dried. This brownish black solid was dissolved in a minimal amount of acetonitrile, and purified by column chromatography on silica using 80:18:2 MeCN:water:sat. KNO$_3$ as the eluant. The tree fractions collected corresponded to the compounds generated by ligand scrambling [bis-(2,2';6',2"-terpyridine)Os(II), bis-(4'-bromo-2,2';6',2"-terpyridine)Os (II), and the desired product]. The second band corresponded to the product; the volume of misfraction was reduced to 50 mL, and ammonium hexafluorophosphate (1 g) in 10 mL of water was added, yielding a brown precipitate. This material was filtered, washed successively with water and ether, and dried, giving 860 mg of product (42% based on 1.06 g of the Os(tpy)Cl$_3$ starting material). $^1$H-NMR (250 MHz, CD$_3$CN): 8.98 (s, 1 H), 8.85 (s, 1 H), 8.75 (d, 2 H, J=8.2 Hz), 8.45 (4 H, J=8.1 Hz), 7.94 (t, 1 H, J=8.2 Hz), 7.77 (q, 4 H, J=5.1 Hz), 7.22 (t, 4 H, J=5.8 Hz), 7.08 (q, 4 H, J=4.9 Hz). HRMS (ESI$^+$) m/z: 881.0282 (calcd for C$_{30}$H$_{21}$N$_6$BrOsPF$_6$ (M-PF$_6$)$^+$ 881.0268).

Example 10

1,3-Di(3,3-dimethylbutoxy)benzene (10)

Triphenyl phosphine (130 g, 0.495 mol) was placed in a three-neck 2-L flask fitted with a mechanical overhead stirrer, a pressure equalizing addition funnel, and a nitrogen inlet. THF (1 L) was added to the flask and cooled to 0° C. with stirring. Diethylazodicarboxylate (89 g, 0.511 mol) was added dropwise over a period of 30 min via the addition funnel; after the addition was complete, the reaction was warmed to room temperature, during which time a white precipitate formed. Resorcinol (25.7 g, 0.183 mol) and 3,3-dimethylbutanol (50.1 g, 0.490 mol) were added, and the mixture was stirred under nitrogen for 24 h. Removal of the volatiles gave an orange oil, which was triturated with ether; a white precipitate formed, which was subsequently filtered and washed with ether. Removal of solvent afforded a crude product which was purified by column chromatography on silica using 9:1 hexanes:ethylacetate as the eluant, giving 34.1 g of pure 1,3-di-(3',3'-dimethylbutoxy)benzene (66.9% yield, based on 25.7 g of the resorcinol starting material). $^1$H NMR (250 MHz, CDCl$_3$): 7.14 (t, 1H, J=9.9 Hz), 6.49 (m, 1H), 6.43 (m, 2H), 3.98 (t, 4H, J=9.2 Hz), 1.70 (t, 4H, J=9.4 Hz), 0.97 (s, 18H). HRMS (ESI$^+$) m/z: 279.2300 (calcd for C$_{18}$H$_{31}$O$_2$ (M+H)$^+$ 279.2324).

Example 11

2,6-Bis(3,3-dimethylbutoxy)benzaldehyde (11)

TMEDA (23.0 g, 0.198 mol), 1,3-di(3,3-dimethylbutoxy)benzene (46.2 g, 0.166 mol) and ether (500 mL) were brought together in a two-neck 1-L flask fitted with a nitrogen inlet and a pressure-equalizing addition funnel. The reaction mixture was cooled to 0° C., and deaerated. n-BuLi (2.5 M solution in hexanes, 0.18 mol) was added dropwise over a period of 30 min via the addition funnel. The mixture was stirred for 3 h, following which that time it was warmed to room temperature. At this point DMF (23.0 g, 0.315 mol) was added dropwise; after 2 h of stirring, the reaction was quenched with water, extracted with ether (4×300 mL), separated, and evaporated. The product was purified by chromatography on silica using 9:1 hexanes:ethyl acetate as the eluant, giving 36.6 g of product (72% yield, based on 46.2 g of the 1,3-di(3,3-dimethylbutoxy)benzene starting material). $^1$H NMR (250 MHz, CDCl$_3$): 10.49 (s, 1H), 7.37 (t, 1H, J=8.5 Hz), 6.52 (d, 2H, J=8.5 Hz), 4.06 (t, 4H, J=7.2 Hz), 1.76 (t, 4H, J=7.2 Hz), 0.96 (s, 18H). HRMS (ESI$^+$) m/z: 329.2107 (calcd for C$_{19}$H$_{30}$O$_3$Na (M+Na)$^+$ 329.2092).

Example 12

5,15-Bis(2',6'-di(3,3-dimethylbutoxy)phenyl)porphyrin (12)

Dipyrrylmethane (3.1 g, 21.2 mmol) and 2,6-bis(3,3-dimethylbutoxy)benzaldehyde (6.3 g, 20.6 mmol) were placed in a freshly opened 4 L bottle of methylene chloride fitted with a septum. The solution was deaerated, and boron trifluoride etherate (200 µL, 1.6 mmol) was added. The mixture was stirred at room temperature for 3 h, following which time it was quenched with DDQ (7.2 g, 31.7 mmol) and stirred for an additional h. Evaporation of the solvent gave a black residue which was redissolved in a minimal amount of methylene chloride, filtered through a plug of silica, and evaporated. The product was purified by chromatography using a hexanes-packed silica column and methylene chloride as the mobile phase. The product was collected as a reddish purple band, giving 2.67 g of compound 12 (30% yield, based on 3.1 g of the dipyrrylmethane starting material). $^1$H NMR (250 MHz, CDCl$_3$): 10.14 (s, 2H), 9.25 (d, 2H, J=4.5 Hz), 8.94 (d, 4H, J=4.6 Hz), 7.71 (t, 2H, J=8.4 Hz), 7.00 (d, 4H, 8.3 Hz), 3.89 (t, 8H, J=7.4 Hz), 0.81 (t, 8H, J=7.4 Hz), 0.29 (s, 36H). HRMS (ESI$^+$) m/z: 863.5496 (calcd for C$_{56}$H$_{71}$N$_4$O$_4$ (M+H)$^+$ 863.5475).

Example 13

5-Bromo-10,20-bis(2',6'-di(3,3-dimethylbutoxy)phenylporphyrin (13)

5,15-Bis(2',6'-di(3,3-dimethylbutoxy)phenyl)porphyrin (1.5 g, 1.74 mmol) was dissolved in chloroform (400 mL) and cooled to 0° C. with stirring. NBS (318 mg, 1.79 mmol) was added, and the reaction stirred at 0° C. for 30 min, following which time it was quenched with acetone (30 mL). Evaporation of the solvent gave a purple solid which was purified by column chromatography on silica using 1:1 chloroform:hexanes as the eluant, giving 800 mg of product which was collected as the second reddish purple band (49% yield, based on 1.5 g of the porphyrin starting material). $^1$H NMR (250 MHz, CDCl$_3$): 9.48 (d, 4H, J=6.1 Hz), 8.75 (d, 4H, J=6.1 Hz), 7.69 (t, 2H, J=10.5 Hz), 6.97 (d, 2H, J=10.6 Hz), 3.88 (t, 8H, J=9.1 Hz), 0.84 (t, 8H, J=9.1 Hz), 0.28 (s, 36H), −2.65 (s, 2H). HRMS (ESI$^{30}$) m/z: 1019.3693 (calcd for C$_{56}$H$_{69}$Br$_2$N$_4$O$_4$ (M+H)$^+$ 1019.3686).

Example 14

5,15-Dibromo-10,20-bis(2',6'-di(3,3-dimethylbutoxy)phenylporphyrin (14)

5,15-Bis(2',6'-di(3,3-dimethylbutoxy)phenyl)porphyrin (1.5 g, 1.74 mmol) was dissolved in chloroform (400 mL) and cooled to 0° C. with stirring. NBS (635 mg, 3.57 mmol) was added, and the reaction stirred at 0° C. for 30 min, following which time it was quenched with acetone (30 mL). Evaporation of the solvent gave a purple solid which was purified by column chromatography on silica using 1:1 chloroform:hexanes as the eluant, giving 1.68 g of product which was collected as a reddish purple band. (95% yield, based on 1.5 g of the porphyrin starting material). $^1$H NMR (250 MHz, CDCl$_3$): 9.48 (d, 4H, J=6.1 Hz), 8.75 (d, 4H, J=6.1 Hz), 7.69 (t, 2H, J=10.5 Hz), 6.97 (d, 2H, J=10.6 Hz), 3.88 (t, 8H, J=9.1 Hz), 0.84 (t, 8H, J=9.1 Hz), 0.28 (s, 36H), −2.65 (s, 2H). HRMS (ESI$^+$) m/z: 1019.3693 (calcd for C$_{56}$H$_{69}$Br$_2$N$_4$O$_4$ (M+H)$^+$ 1019.3686).

Example 15

[5-Bromo-10,20-di(2',6'-bis(3,3-dimethylbutoxy)phenyl)porphinato]zinc(II) (15)

A 1 L flask was charged with chloroform (400 mL), compound 13 (1.40 g, 1.49 mmol), zinc(II)acetate (3 g, 13 mmol) and refluxed for 2 h and cooled to room temperature. The solution was washed with water, separated, and evaporated, giving a purple residue. This material was redissolved in 7:1 hexanes:THF, and purified by column chromatography on silica using the identical solvent system as the eluant. The product was collected as a reddish purple band, giving 1.42 g of product (95% yield, based on 1.40 g of the porphyrin starting material). $^1$H NMR (250 MHz, CDCl$_3$:d$_5$-pyridine 20:1): 9.89 (s, 1 H), 9.59 (d, 2 H, J=4.6 Hz), 9.14 (d, 2 H, J=4. Hz), 8.88 (d, 2 H, J=4.5 Hz), 8.87 (d, 2 H, J=4.8 Hz), 7.70 (t, 2 H, J=8.3 Hz), 7.01 (d, 4 H, J=8.4 Hz), 3.88 (t, 8 H, J=7.7 Hz), 0.76 (t, 8 H, J=7.6 Hz), 0.34 (s, 36 H). HRMS (ESI$^+$) m/z: 1003.3712 (calcd for C$_{56}$H$_{68}$BrN$_4$O$_4$ZnBr (M+H)$^+$ 1003.3715).

Example 16

[5,15-Dibromo-10,20-di(2',6'-bis(3,3-dimethylbutoxy)phenyl)porphinato]zinc(II) (16)

A 1 L flask was charged with chloroform (400 mL), compound 14 (1.68 g, 1.64 mmol), zinc(II)acetate (3 g, 13 mmol) and refluxed for 2 h. The solution was cooled to room temperature, washed with water, separated, and evaporated, giving a purple residue. This material was dissolved 7:1 hexanes:THF, and purified by column chromatography on silica using the identical solvent system as the eluant. The product was collected as a reddish purple band, giving 1.69 g of compound 16 (95% yield, based on 1.68 g of the porphyrin starting material). $^1$H NMR (250 MHz, CDCl$_3$:d$_5$-pyridine 20:1): 9.58 (d, 4H, J=4.4 Hz), 8.82 (d, 4H, J=4.9 Hz), 7.69 (t, 2H, 8.4 Hz), 6.98 (d, 4H, J=8.4 Hz), 3.88 (t, 8H, J=7.5 Hz), 0.80 (t, 8H, J=7.5 Hz), 0.29 (s, 36H). LRMS (ESI$^+$) m/z: 1103.1 (calcd for C$_{56}$H$_{66}$Br$_2$N$_4$O$_4$ZnNa (M+Na)$^+$ 1103.3). (ESI$^-$) m/z: 1114.7 (calcd for C$_{56}$H$_{66}$Br$_2$N$_4$O$_4$ZnCl (M+Cl)$^-$ 1115.2).

Example 17

[5-((Triisopropylsilyl)ethynyl)-10,20-di(2',6'-bis(3,3-dimethylbutoxy)phenyl)porphinato]zinc(II) (17)

A 100 mL Schlenk storage tube containing [5-bromo-10,20-di(2',6'-bis(3,3-dimethylbutoxy)phenyl)porphinato]zinc (II) (1052 mg, 1.05 mmol), Pd(PPh$_3$)$_4$ (115 mg, 0.10 mmol), and THF (50 mL) was degassed via three freeze-pump-thaw cycles. A five-fold molar excess of the triisopropylsilylethynylzinc chloride reagent was transferred to the flask, and the mixture was heated to 60° C. for 16 h. The course of the reaction was monitored by TLC. The reaction mixture was cooled to room temperature and adsorbed to silica gel (150 mL). The product was purified by column chromatography using 7:1 hexanes:THF as the eluant, giving 1.08 g of compound 16 (93% yield, based on 504 mg of the [5-bromo-10,20-di(2',6'-bis(3,3-dimethylbutoxy)phenyl)porphinato]zinc (II) starting material). $^1$H NMR (250 MHz, CDCl$_3$): 10.02 (s, 1 H), 9.72 (d, 2 H, J=4.5 Hz), 9.20 (d, 2 H, J=4.5 Hz), 8.91 (pt, 4 H, J=4.7 Hz), 7.68 (t, 2 H, J=8.3 Hz), 6.99 (d, 4 H, J=8.4 Hz), 3.88 (t, 8 H, J=7.4 Hz), 1.43 (m, 21 H), 0.27 (s, 36H). LRMS (ESI$^+$) m/z: 1127.2 (calcd for C$_{67}$H$_{88}$N$_4$O$_4$SiZnNa (M+Na)$^+$ 1127.6).

Example 18

[5-Ethynyl-10,20-di(2',6'-bis(3,3-dimethylbutoxy)phenyl)porphinato]zinc(II) (18)

[5-((Triisopropylsilyl)ethynyl)-10,20-di(2',6'-bis(3,3-dimethylbutoxy)phenyl)porphinato]zinc(II) (860 mg, 0.78 mmol) was dissolved in THF (30 mL). TBAF (1.6 mL, 1 M in THF) was added, and the reaction was stirred for 5 min, after which time TLC analysis showed complete formation of the product and consumption of the starting material. At this point, the reaction mixture was quenched with water (50 mL), extracted with CHCl$_3$, and evaporated. The residue was redissolved in THF, adsorbed to 50 g of silica, and purified by column chromatography using 5:1 hexanes:THF as the eluant, giving 675 mg of product (91% yield, based on 860 mg of the [5-((triisopropyl)ethynyl)-10,20-di(2',6'-bis(3,3-dimethylbutoxy)phenyl)porphinato]zinc(II) starting material). $^1$H NMR (250 MHz, CDCl$_3$:d$_5$-pyridine 20:1): 9.91 (s, 1 H), 9.59 (d, 2 H, J=4.5 Hz), 9.12 (d, 2H, J=4.5 Hz), 8.87 (d, 2 H, J=4.6 Hz), 8.83 (d, 2 H, J=4.5 Hz), 7.68 (t, 2 H, J=8.4 Hz), 7.00 (d, 4 H, J=8.4 Hz), 4.04 (s, 1 H), 3.87 (t, 8 H, J=7.6 Hz), 0.75 (t, 8 H, J=7.5 Hz), 0.32 (s, 36H). HRMS (ESI$^+$) m/z: 949.4651 (calcd for C$_{58}$H$_{69}$N$_4$O$_4$Zn (M+H)$^+$ 949.4610).

Example 19

[5,15-Bis((trimethylsilyl)ethynyl)-10,20-di(2',6'-bis(3,3-dimethylbutoxy)phenyl)porphinato]zinc(II) (19)

[5,15-Dibromo-10,20-di(2',6'-bis(3,3-dimethylbutoxy)phenyl)porphinato]zinc(II) (830 mg, 0.77 mmol), trimethylsilylethynylzinc chloride in THF (20 mL, 0.45 M), and THF (40 mL) were brought together in an oven-dried 100 mL Schlenk tube. The solution was degassed via three freeze-pump-thaw cycles, following which Pd(PPh$_3$)$_4$ (100 mg, 0.09 mmol) was added. The reaction was stirred under N$_2$ at 60° C. for 24 h, cooled to room temperature, and evaporated. The residue was redissolved in THF and adsorbed to 100 g of silica. The product was purified by column chromatography on silica using 85:15 hexanes:THF as the eluant. The product was collected as a greenish purple band, giving 800 mg of product (93% yield, based on 830 mg of the porphyrin starting material). $^1$H NMR (250 MHz, CDCl$_3$): 9.57 (d, 4 H, J=4.6 Hz), 8.80 (d, 4 H, J=4.6 Hz), 7.69 (t, 2 H, J=8.4 Hz), 6.99 (t, 4 H, J=8.5 Hz), 3.89 (t, 8 H, J=7.4 Hz), 0.81 (t, 8 H, J=7.5 Hz), 0.59 (s, 18 H), 0.32 (s, 36 H). LRMS (ESI$^+$) m/z: 1117.2 (calcd for C$_{66}$H$_{84}$N$_4$O$_4$Si$_2$Zn (M)$^+$ 1116.5). (ESI$^-$) m/z: 1151.1 (calcd for C$_{66}$H$_{84}$N$_4$O$_4$Si$_2$ZnCl (M+Cl)$^-$ 1151.5).

Example 20

[5,15-Bis(ethynyl)-10,20-di(2',6'-bis(3,3-dimethylbutoxy)phenyl)porphinato]zinc(II) (20)

Compound 19 (500 mg, 0.45 mmol) was dissolved in THF (30 mL). TBAF (1.0 mL, 1M in THF) was added and the reaction was stirred for 5 min, after which time TLC analysis showed complete formation of the product and consumption of the starting material. At which point, the reaction mixture was quenched with water (50 mL), extracted with CHCl$_3$, and evaporated. The residue was redissolved in THF, adsorbed to 50 g of silica, and purified by column chromatography using 85:15 hexanes:THF as the eluant, giving 410 mg of product (94% yield, based on 500 mg of the [5,15-bis((trimethylsilyl)ethynyl)-10,20-di(2',6'-bis(3,3-dimethylbutoxy)phenyl)porphinato]zinc(II) starting material). $^1$H NMR (250 MHz, CDCl$_3$:d$_5$-pyridine 20:1): 9.51 (d, 4 H, J=4.6 Hz), 8.77 (d, 4 H, J=4.6 Hz), 7.67 (t, 2 H, J=8.3 Hz), 6.98 (d, 4 H, J=8.5 Hz), 4.04 (s, 2 H), 3.89 (t, 8 H, J=7.6 Hz), 0.76 (t, 8 H, J=7.6 Hz), 0.34 (s, 36 H). HRMS (ESI$^+$) m/z: 973.4615 (calcd for C$_{60}$H$_{69}$N$_4$O$_4$Zn (M+H)$^+$ 973.4610).

Example 21

[5-(4'-Ethynyl-2,2';6',2''-terpyridyl)-10,20-di(2',6'-bis-(3,3-dimethylbutoxy)phenyl)porphinato]zinc(II) (21)

[5-Ethynyl-10,20-di(2',6'-bis(3,3-dimethylbutoxy)phenyl)porphinato]zinc(II) (155 mg, 0.16 mmol), 4'-bromo-2,2';6',2''-terpyridine (280 mg, 0.90 mmol), diisopropylamine (8 mL), and THF (30 mL) were brought together in an oven-dried 100 mL Schlenk tube. The solution was degassed via three freeze-pump-thaw cycles following which Pd(PPh$_3$)$_4$ (30 mg, 0.026 mmol) and CuI (8 mg, 0.042 mmol) were added. The reaction was stirred under N$_2$ at 70° C. for 20 h, cooled to room temperature, and evaporated. The product was purified by column chromatography on neutral alumina using 3:2 hexanes:THF as the eluant. The product eluted as a green band; the volatiles were evaporated and the residual solid was further purified on a size exclusion column (SX-1 biobeads) utilizing a THF eluant. A second round of chromatography on neutral alumina using 1:1 THF:hexanes as the eluant, gave 126 mg of pure compound 21 (67% yield, based on 155 mg of the [5-ethynyl-10,20-di(2',6'-bis(3,3-dimethylbutoxy)phenyl)porphinato]zinc(II) starting material). $^1$H-NMR (250 MHz, pyridine-d$_5$) 10.14 (s, 1 H), 10.08 (d, 2 H, J=4.5 Hz), 9.36 (d, 2 H, J=4.6 Hz), 9.34 (d, 2 H, J=4.5 Hz), 9.31 (s, 2 H), 9.36 (d, 2 H, J=4.4 Hz), 8.89 (m, 4 H), 8.06 (t, 2 H, J=8.3 Hz), 7.94 (dt, 2 H, J=7.7 Hz, 1.9 Hz), 7.38 (m, 6 H), 4.13 (t, 8 H, J=7.1 Hz), 0.93 (t, 8 H, J=7.5 Hz), 0.33 (s, 36 H).

Example 22

[5,15-Bis(4'-ethynyl-2,2';6',2"-terpyridyl)-10,20-di (2',6'-bis-(3,3-dimethylbutoxy)phenyl)porphinato] zinc(II) (22)

[5,15-Diethynyl-10,20-di(2',6'-bis(3,3-dimethylbutoxy) phenyl)porphinato]zinc(II) (123 mg, 0.13 mmol), 4'-bromo-2,2';6',2"-terpyridine (330 mg, 1.06 mmol), diisopropylamine (8 mL), and THF (30 mL) were brought together in an oven-dried 100 mL Schlenk tube. The solution was degassed via three freeze-pump-thaw cycles following which Pd(PPh$_3$)$_4$ (30 mg, 0.026 mmol) and CuI (10 mg, 0.053 mmol) were added. The reaction was stirred under N$_2$ at 70° C. for 20 h, cooled to room temperature, and evaporated. The product was purified by column chromatography on neutral alumina using 7:3 hexanes:THF as the eluant. The product eluted as a purplish green band; the volatiles were evaporated and the residual solid was further purified on a size exclusion column (SX-1 biobeads) utilizing a THF eluant. A second round of chromatography on neutral alumina using 3:2 hexanes:THF as the eluant, gave 97 mg of pure compound 22 (52% yield, based on 123 mg of the [5,15-diethynyl-10,20-di(2',6'-bis(3, 3-dimethylbutoxy)phenyl)porphinato]zinc(II) starting material). $^1$H-NMR (250 MHz, pyridine-d$_5$) 10.01 (d, 4 H, J=4.5 Hz), 9.30 (s, 4 H), 9.25 (d, 4 H, J=4.5 Hz), 8.90 (8 H, m), 8.08 (t, 2 H, J=8.3 Hz), 7.94 (dt, 4 H, J=7.7 Hz, 1.9 Hz), 7.40 (8 H, m), 4.18 (t, 8 H, J=7.5 Hz), 0.99 (t, 8 H, J=7.5 Hz), 0.36 (s, 36 H).

Example 23

[5-Bromo-15-triisopropylsilylethynyl-10,20-di(2',6'-bis-(3,3-dimethylbutoxy)phenyl)porphinato]zinc(II) (23)

[5-Triisopropylsilylethynyl-10,20-di(2',6'-bis-(3,3-dimethyl-1-butoxy)phenyl)porphinato]zinc(II) (1.65 g, 1.5 mmol) was dissolved in 200 mL of a 95:5 chloroform:pyridine solvent mixture. The greenish purple solution was cooled to 0° C., and N-bromo-succinimide (270 mg, 1.52 mmol) was added in one portion. The reaction was stirred at 0° C. for 30 min and monitored by TLC (4:1 hexanes:THF). Acetone (30 mL) was added at the reaction endpoint, and the mixture was stirred for an additional 20 min. Following evaporation of volatiles, the residue was purified by column chromatography on silica using 15:85 hexanes:THF as the eluant. The product was collected as a greenish purple band, giving 1.52 g of compound 23 (85% yield based on 1.65 g of the porphyrin starting material). $^1$H-NMR (250 MHz, CDCl$_3$): 9.63 (d, 2 H, J=4.9 Hz), 9.56 (d, 2 H, J=4.5 Hz), 8.81 (pt, 4 H, J=5.5 Hz), 7.68 (t, 2 H, J=8.2 Hz), 6.98 (d, 4 H, J=8.4 Hz), 3.89 (t, 8 H, J=7.5 Hz), 1.43 (m, 21 H), 0.80 (t, 8 H, J=7.5 Hz), 0.36 (s, 36 H). LRMS (ESI$^+$) m/z: 1182.8 (calcd for C$_{67}$H$_{88}$N$_4$O$_4$BrSiZn (M+H)$^+$ 1182.5). (ESI$^+$) m/z: 1205.0 (calcd for C$_{67}$H$_{87}$N$_4$O$_4$BrSiZnNa (M+Na)$^+$ 1205.5). (ESI$^-$) m/z: 1217.5 (calcd for C$_{67}$H$_{87}$N$_4$O$_4$BrSiZnCl (M+Cl)$^-$ 1217.5).

Example 24

Ruthenium(II) 5-[4'-Ethynyl-(2,2';6',2"-terpyridinyl)]-15-(triisopropylsilyl)ethynyl)-bis[10,20-di(2', 6'-bis(3,3-dimethylbutoxy)phenyl)porphinato]zinc (II)-(2,2';6',2"-terpyridine)$^{2+}$bis-hexafluorophosphate [Ru(tpy)$_2$-C≡C—PZn—C≡C-TIPS] (24)

Compound 23 (300 mg, 0.25 mmol), [Ru(tpy)(4'-ethynyl-tpy)](PF$_6$)$_2$ (440 mg, 0.5 mmol), diisopropylamine (8 mL), THF (50 mL) and acetonitrile (80 mL) were brought together in an oven-dried 350 mL Schlenk tube. The solution was degassed via three freeze-pump-thaw cycles following which Pd(PPh$_3$)$_4$ (60 mg, 0.05 mmol) and CuI (20 mg, 0.11 mmol) were added. The reaction was stirred under N$_2$ at 50° C. for 24 h, cooled to room temperature, and evaporated. The product was purified by column chromatography on silica using 80:18:2 acetonitrile:water:saturated KNO$_3$ as the eluant. The product eluted as a brownish green band; the volume of the product fraction was reduced to 50 mL, and ammonium hexafluorophosphate (1 g) in 10 mL of water was added, producing a brown precipitate. The product was filtered, washed successively with water and ether, and dried to give 400 mg of compound 24 as the hexafluorophosphate salt (81% yield, based on 300 mg of the compound 23 starting material). $^1$H-NMR (250 MHz, CD$_3$CN): 9.93 (d, 2 H, J=4.5 Hz), 9.58 (d, 2 H, J=4.6 Hz), 9.36 (s, 2 H), 8.91 (d, 2 H, J=4.7 Hz), 8.76 (m, 6 H), 8.48 (m, 5 H), 8.01 (m, 2 H), 7.98 (m, 2 H), 7.80 (t, 2 H, J=8.4 Hz), 7.54 (d, 2 H, J=5.3 Hz), 7.40 (d, 2 H, J=4.8 Hz), 7.18 (m, 6 H), 3.99 (t, 8 H, J=7.0 Hz), 1.42 (m, 21 H), 0.80 (t, 8 H, J=7.0 Hz), 0.18 (s, 36 H). LRMS (ESI$^+$) m/z: 1841.4 (calcd for C$_{99}$H$_{108}$N$_{10}$O$_4$RuSiZnP$_2$F$_{12}$ (M-PF$_6$)$^+$ 1841.5). m/z: 1695.6 (calcd for C$_{99}$H$_{108}$N$_{10}$O$_4$RuSiZn (M-2PF$_6$)$^+$ 1696.5). m/z: 848.3 (calcd for C$_{99}$H$_{108}$N$_{10}$O$_4$RuSiZn (M-2PF$_6$)$^{2+}$ 848.3).

Example 25

Ruthenium(II) 5-[4'-Ethynyl-(2,2';6',2"-terpyridinyl)]-15-ethynyl-bis[10,20-di(2',6'-bis(3,3-dimethylbutoxy)phenyl)porphinato]zinc(II)-(2,2';6',2"-terpyridine)$^{2+}$ bis-hexafluorophosphate [Ru(tpy)$_2$-C≡C—PZn—C≡C—H] (25)

Compound 24 (368 mg, 0.19 mmol) was dissolved in MeCN (30 mL). TBAF (250 µL, 1M in THF) was added and the reaction was stirred for 5 min, after which time TLC analysis showed complete formation of the product and consumption of the starting material. At which point, the reaction mixture was quenched with water (50 mL), purified by column chromatography on silica using 80:18:2 acetonitrile:water:saturated KNO$_3$ as the eluant. The product eluted as a brownish green band; the volume of the product fraction was reduced to 50 mL, and ammonium hexafluorophosphate (1 g) in 10 mL of water was added, producing a brown precipitate. The product was filtered, washed successively with water and ether, and dried to give 265 mg of compound 25 as the hexafluorophosphate salt (78% yield, based on 368 mg of the compound 24 starting material). $^1$H-NMR (250 MHz, CD$_3$CN): 9.55 (d, 2 H, J=4.5 Hz), 9.54 (d, 2 H, J=4.5 Hz), 9.36 (s, 2 H), 8.93 (d, 2 H, J=4.8 Hz), 8.76 (m, 6H), 8.47 (m, 5 H), 7.99 (m, 2 H), 7.89 (m, 2 H), 7.80 (t, 2 H, J=8.4 Hz), 7.55 (d, 2 H, J=4.8 Hz), 7.40 (d, 2 H, J=4.7 Hz), 7.20 (m, 6 H), 4.46 (s, 1 H), 3.99 (t, 8 H, J=7.0 Hz), 0.81 (t, 8 H, J=7.0 Hz), 0.17 (s, 36 H). LRMS (ESI$^+$) m/z: 771.4 (calcd for C$_{90}$H$_{88}$N$_{10}$O$_4$RuZn (M-2PF$_6$)$^{2+}$ 770.1).

Example 26

Ruthenium(II)-5-[4'-Ethynyl-(2,2';6',2"-terpyridinyl) (2,2';6',2"-terpyridine)]-osmium(II)-15-[4'ethynyl-(2, 2';6',2"-terpyridinyl)(2,2';6',2"-terpyridine)]bis[10, 20-di(2',6'-bis(3,3-dimethylbutoxy)phenyl) porphinato]zinc(II)$^{4+}$ tetrakis-hexafluorophosphate [Ru(tpy)$_2$-C≡C—PZn—C≡C—Os(tpy)$_2$] (26)

Compound 25 (226 mg, 0.12 mmol), [Os(tpy)(4'-Br-tpy)] (PF$_6$)$_2$ (363 mg, 0.35 mmol), diisopropylamine (6 mL), THF (30 mL) and acetonitrile (100 mL) were brought together in an oven-dried 350 mL Schlenk tube. The solution was degassed via three freeze-pump-thaw cycles following which Pd(PPh$_3$)$_4$ (60 mg, 0.05 mmol) and CuI (15 mg, 0.08 mmol) were added. The reaction was stirred under N$_2$ at 50° C. for 24 h, cooled to room temperature, and evaporated. The product was purified by column chromatography on silica using 80:18:2 acetonitrile: water:saturated KNO$_3$ as the eluant. The product eluted as a brownish green band; the volume of the product fraction was reduced to 50 mL and ammonium hexafluorophosphate (1 g) in 10 mL of water was added, producing a brown precipitate. The product was filtered, washed successively with water and ether, and dried to give 196 mg of compound 26 as the hexafluorophosphate salt (59% yield based on 226 mg of the compound 25 starting material). $^1$H-NMR (250 MHz, CD$_3$CN): 9.98 (d, 2 H, J=4.5 Hz), 9.97 (d, 2 H, J=4.8 Hz), 9.39 (s, 2 H), 9.38 (s, 2H), 8.95 (d, 2 H, J=4.4 Hz), 8.94 (d, 2 H, J=4.9 Hz), 8.79 (m, 8 H), 8.50 (m, 5 H), 7.91 (m, 15 H), 7.55 (d, 2 H, J=5.5 Hz), 7.40 (m, 2 H), 7.20 (m, 12 H), 4.04 (t, 8 H, J=6.9 Hz), 0.88 (t, 8 H, J=6.9 Hz), 0.19 (s, 36 H). LRMS (ESI$^+$) m/z: 2627.8 (calcd for C$_{120}$H$_{108}$N$_{106}$O$_4$OsRuZnP$_3$F$_{18}$ (M-3PF$_6$)$^+$ 2629.8). m/z: 1241.7 (calc for C$_{120}$H$_{108}$N$_{16}$O$_4$RuOsZnP$_2$F$_{12}$ (M-2PF$_6$)$^{2+}$ 1242.4). m/z: 1096.4 (calc for C$_{120}$H$_{108}$N$_{16}$O$_4$RuOsZn (M-4PF$_6$)$^{2+}$ 1097.4). m/z: 731.1 (calcd for C$_{120}$H$_{108}$N$_{16}$O$_4$RuOsZn (M-4PF$_6$)$^{3+}$ 731.6).

Example 27

Molecular First Order Hyperpolarizability

The molecular first order hyperpolarizability. [β$_λ$ Values (×10$^{-30}$ esu)] were determined via Hyper Raleigh Light Scattering (HRS) for Ru—PZn (compound 1 of Example 1), Os—PZn (compound 2 of Example 2) and Ru—PZn—Os (compound 26 of Example 26), as well as for Ruthenium(II) [5-(4'-Ethynyl-(2,2';6',2"-terpyridinyl)-15-(4'-nitrophenyl) ethynyl-10,20-bis(2',6'-bis(3,3-dimethyl-1-butyloxy)phenyl)porphinato]zinc(II)-(2,2';6,2"-terpyridine)$^{2+}$ Bis-hexafluorophosphate [Ru—PZn-A], Osmium(II) [5-(4'-Ethynyl-(2,2';6',2"-terpyridinyl)-15-(4'-nitrophenyl)ethynyl-10,20-bis(2',6'-bis(3,3-dimethyl-1-butyloxy)phenyl)porphinato]zinc(II)-(2,2';6,2"-terpyridine)$^{2+}$ Bis-hexafluorophosphate [Os—Zn-A] and [5-(4'-dimethylaminophenylethynyl)-15-(4'-nitrophenylethynyl)-10, 20-diphenylporphinato]zinc(II) [D-PZn-A]. Ru—PZn-A and Os—PZn-A were prepared according to the methods described in Uyeda et al., *J. Am. Chem. Soc.*, 124, 13806-13813 (2002), the disclosure of which is incorporated herein by reference in its entirety. D-PZn-A was prepared according to Example 2 of the above-referenced U.S. Pat. No. 5,783, 306. Values were obtained at 20° C. in dichloromethane. Different modulation frequencies were used and β$_λ$ values were measured independent of frequency modulation of the fundamental beam (DC to 960 MHz) to to verify that multiphoton fluorescence contributions did not contribute to observed HRS signals. The results are set forth in Table I.

TABLE I

Dynamic Hyperpolarizabilities [β$_λ$ Values, (×10$^{-30}$ esu] Determined via HRS

| Compound | β$_{800}$ | β$_{1064}$ | β$_{1300}$ |
|---|---|---|---|
| Ru—PZn | <50[a] | 2100 | 5100 |
| Os—PZn | <50 | 2600 | <50 |
| Ru—PZn-A | 220 | 4000 | 2400 |
| Os—PZn-A | 250 | 5000 | <50 |
| Ru—PZn—OS | 240 | 4500 | 860 |
| D—PZn-A | 5142 | 4933 | [b] |

[a]Upper limit corresponds to the smallest HRS signal that can be measured accurately.
[b]Not measured.

Figures 18A, 18B, 18C:
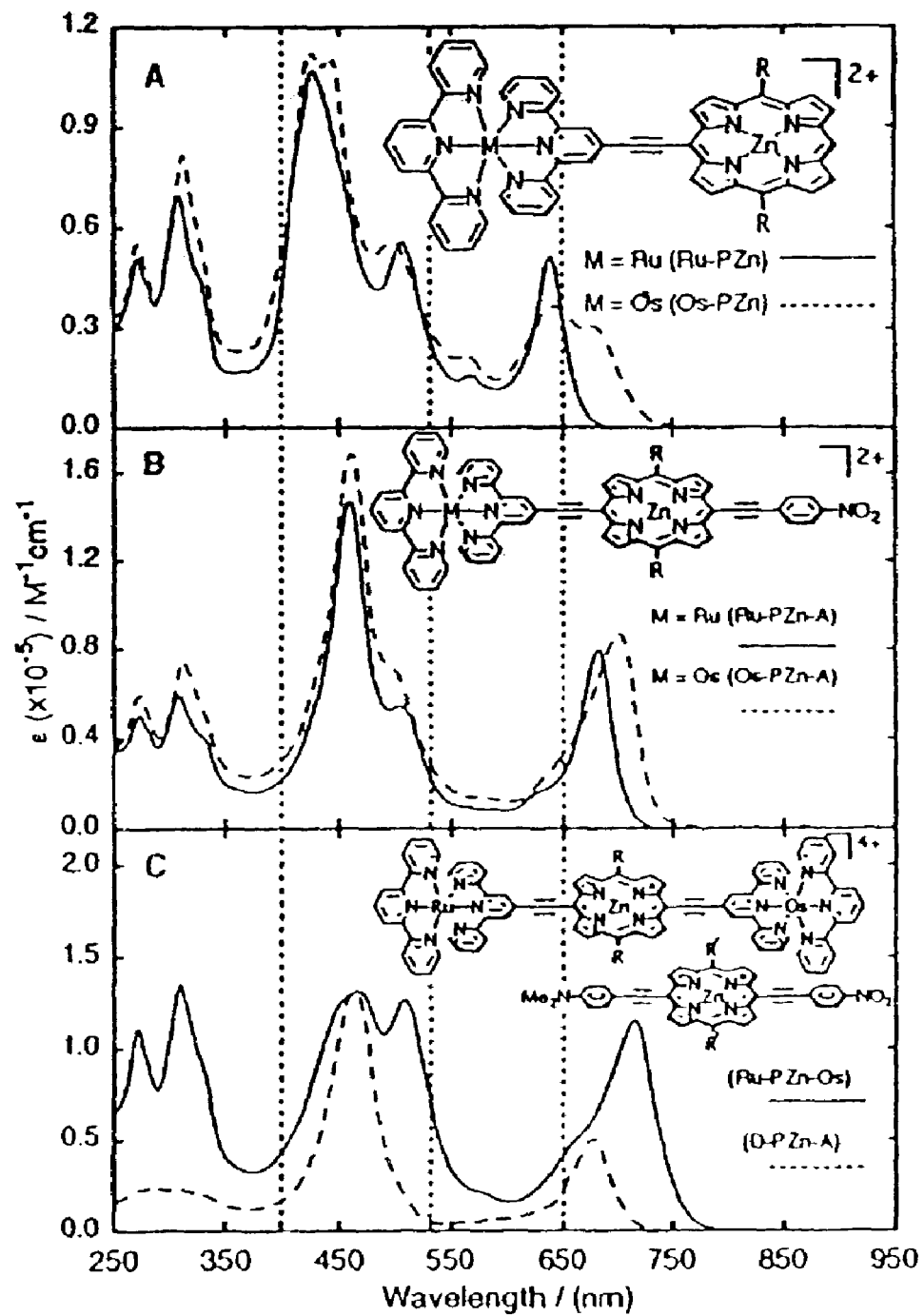

Comparative electronic absorption spectra for the compounds is shown in FIGS. 18A-18C. The dashed vertical lines indicate the wavelengths corresponding to the respective second harmonics of the fundament 830, 1064 and 1300 nm incident radiation. The spectra were obtained at 20° C. using CH$_3$CN as the solvent for Os— and Ru-containing compounds and THF as the solvent for D-PZn-A. These data illustrate that the highly polarizable porphyrinic component and metal pyrridyl complexes serve as integral donor and acceptor moieties.

The FIGS. 18A-18C electronic spectra for Ru—PZ-n, Os—PZn, Ru—PZn-A, Os—PZn-A and Ru—PZn—Os evince strong mixing of PZn-based oscillator strength with metal polypyrridyl charge-resonance bands and display a variety of new low energy electronic transitions that feature significant μ$^2_{ge}$ values and large extinction coefficients. Two aspects of these electronic spectra are particularly noteworthy: (1) they differ markedly from those characteristic of monomeric ethyne-elaborated PZn and Ru(tpy)$_2$ chromophores; and (2) they display an unusual degree of spectral coverage of the 250-750 nm energy domain. The extinction coefficient of Ru—PZn—Os's absorption minimum over this wavelength range (at ~610 nm) exceeds 15,000 M$^{-1}$ cm$^{-1}$. The optical spectra of FIGS. 8-12 further indicate that the building block Ru/Os— and ligand-derived electronic transitions figure prominently in the coupled oscillator photophysics manifest by the Ru—PZn, Os—PZn, Ru—PZn-A, Os—PZn-A and Ru—PZn—OS supermolecules.

The Nonlinear Optical property trends shown in Table I are unusual. The HRS data show that for Ru—PZn, the absolute magnitude of the dynamic hyperpolarizability (|β$_{80}$|) increases with increasing λ$_{inc}$ (800→1064→1300 nm). Structurally related Os—PZn displays a |β$_λ$| maximum at 1064 nm and β$_λ$s<50×10$^{-30}$ esu at 800 and 1300 nm. Ru—PZn-A and Ru—PZn—Os express modest β$_{80}$ values for incident radiation at 800 nm, large β$_λ$s at 1064 nm, and β$_λ$s of 2400 and 860×10$^{-30}$ esu, respectively at 1300 nm. The λ$_{inc}$-dependent trend in β$_λ$ values for Os—PZn-A resembles that observed for Os—PZn, with the large observed β$_{1064}$ value diminishing to approximately zero at λ$_{inc}$=1300 nm.

While NLO response frequency dispersion effects driven by the presence of multiple CT transitions undoubtedly play a role in determining the magnitudes of β$_{80}$ listed in Table I, the nature of the extensive mixing of B, Q and CT electronic states evinced for Ru—PZn, Os—PZn, Ru—PZn-A, Os—PZN-A and Ru—PZN—Os in FIGS. 18A-18C is considerably more complex relative to that manifested in D-PZn-A. This derives from the fact that these species possess at least three redox activecomponents (metal, tpy and PZn). Cyclic voltammetric data for these compounds is shown in FIGS. 13-16.

Oxidative and reductive electrochemical data indicate that at least for Ru—PZn, Os—PZn, Ru—PZn-A and Os—PZn-A, the observed anodic and cathodic potentiometric responses trace their genesis to established metal polypyridyl- and PZn-redox processes, indicating that the singly, doubly, and triply oxidized and reduced ground states of these species correspond to cation and anion states that are largely localized on the building block chromophores. These potentiometric data permit a preliminary analysis of the observed frequency dispersion effects in the NLO response of these species, which reveals that compounds can be designed with B- and Q-state derived $\beta_0$ values selected to have the same or opposite sign. Because the sign of the resonance enhancement factor is frequency dependent, appropriate engineering of the relative contributions of these CT states at a given wavelength provides a new means to regulate the magnitude of dynamic hyperpolarizabilities and, thus, may enable the development of novel materials with enhanced and more selective electrooptic and NLO properties.

In view of the foregoing examples, the present invention thus provides the ability to exploit coupled oscillator photophysics and metal-mediated cross-coupling to elaborate high $\beta_0$ supermolecules. The present invention also provides high-stability inorganic electron-donor moieties that constitute an attractive alternative to electron releasing dialkyl- and diarylamino groups, the most commonly used donor moieties in a wide range of established NLO dyes and long recognized to be the moiety that often limits dye thermal stability. Finally, given the NLO response exemplified by Ru—PZn and the fact that its $\beta_\lambda$ value determined at 1300 nm exceeds by a factor of 2.5 that determined for any other chromophore at this energy, the present invention also provides extraordinarily large $\beta_\lambda$ chromophores at telecommunications relevant wavelengths.

The foregoing examples and description of the preferred embodiment should be taken as illustrating, rather than as limiting, the present invention as defined by the claims. As those skilled in the art will appreciate, numerous changes and modifications can be made to the preferred embodiments of the invention without departing from the spirit of the invention. It is intended that all such variations fall within the scope of the invention.

The entire disclosure of each publication cited herein is hereby incorporated by reference.

What is claimed is:

1. A compound comprising Formula I:

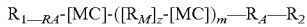

$$R_1{-}_{R_A}\text{-[MC]-([}R_M\text{]}_z\text{-[MC])}_m\text{-}R_A\text{-}R_2$$

wherein:
each MC is, independently, a conjugated macrocycle;
each $R_A$ is independently selected from the group consisting of a covalent bond, alkenyls having 2 to about 20 carbon atoms, cumulenyls having 4 to about 14 carbon atoms and alkynyls having 2 to about 20 carbon atoms;
each $R_M$ is independently selected from the group consisting of alkyls having 1 to about 20 carbon atoms, alkenyls having 2 to about 20 carbon atoms, cumulenyls having 4 to about 14 carbon atoms, alkynyls having 2 to about 20 carbon atoms, aryls having 3 to about 50 carbon atoms, arylalkynyls having 8 to about 24 carbon atoms, arylalkenyls having 8 to about 24 carbon atoms, unsaturated heterocyclos having 4 to about 24 carbon atoms, heteroaryls having 2 to about 50 carbon atoms, unsaturated heterocycloalkenyls, unsaturated heterocycloalkynyls and heteroarylalkynyls;

$R_1$ is selected from the group consisting of H, halo, -protecting groups, organic electron donor groups and inorganic electron donor moieties; and $R_2$ is selected from the group consisting of H, halo, protecting groups, organic electron-accepting groups and inorganic electron-accepting moieties, wherein at least one of $R_1$ and $R_1$ is an inorganic moiety comprising at least one metal atom or metalloid atom, provided said inorganic moiety is not —Pd(Ph$_3$)$_2$Br;
m is 0 to about 50; and
z is 0 or 1.

2. The compound of claim 1 wherein said conjugated macrocycle is complexed with metal atom $M^1$.

3. The compound of claim 2 wherein $M^1$ is zinc.

4. The compound of claim 1 wherein said compound is neutral.

5. The compound of claim 1 wherein said inorganic moiety comprises a metal complex comprising a transition metal.

6. The compound of claim 5 wherein said metal complex comprises a Group 8 transition metal.

7. The compound of claim 5 wherein said metal complex comprises a transition metal selected from the group consisting of Ru, Os, Rh and Pt.

8. The compound of claim 1 wherein both $R^1$ and $R^2$ are inorganic moieties.

9. The compound of claim 8 wherein $R^1$ and $R^2$ are different inorganic moieties.

10. The compound of claim 1 wherein said conjugated macrocycle is porphyrin.

11. The compound of claim 1 comprising one or more substituents that inhibit aggregation of said compound in the bulk phase.

12. The compound of claim 11 wherein said one or more substituents is attached to said conjugated macrocycle.

13. A compound comprising Formula II or III

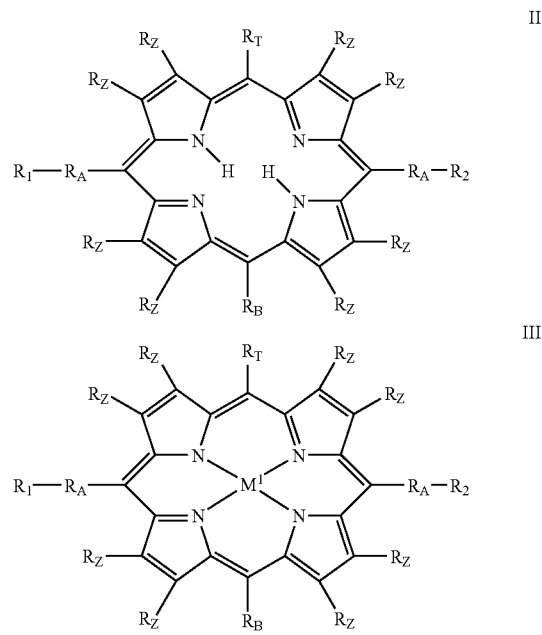

wherein:
$M^1$ is a metal atom;
each $R_A$ is independently selected from the group consisting of a covalent bond, alkenyls having 2 to about 20 carbon atoms, cumulenyls having 4 to about 14 carbon atoms and alkynyls having 2 to about 20 carbon atoms;

$R_1$ is selected from the group consisting of H, halo, protecting groups, organic electron donor groups and inorganic electron donor moieties and $R_2$ is selected from the group consisting of H, halo, protecting groups, organic electron-accepting groups and inorganic electron-accepting moieties, wherein at least one of $R_1$ and $R_2$ is an inorganic moiety comprising at least one metal atom or metalloid atom, provided said inorganic moiety is not —Pd(Ph$_3$)$_2$Br;

each $R_T$ and $R_B$ is independently selected from the group consisting of alkyls having 1 to About 20 carbon atoms, 20. The compound of claim 18 wherein said transition metal is selected from the group consisting of Ru, Os, Rh and Pt.

21. The compound of claim 18 wherein said metal complex comprises a polypyridyl ligand.

22. The compound of claim 21 wherein said polypyridyl ligand is terpyridyl.

23. The compound of claim 13 wherein at least one of said $R_T$, $R_B$, or $R_Z$ is a substituent that inhibits aggregation of said compound in the bulk phase.

24. A compound comprising Formula IV or V

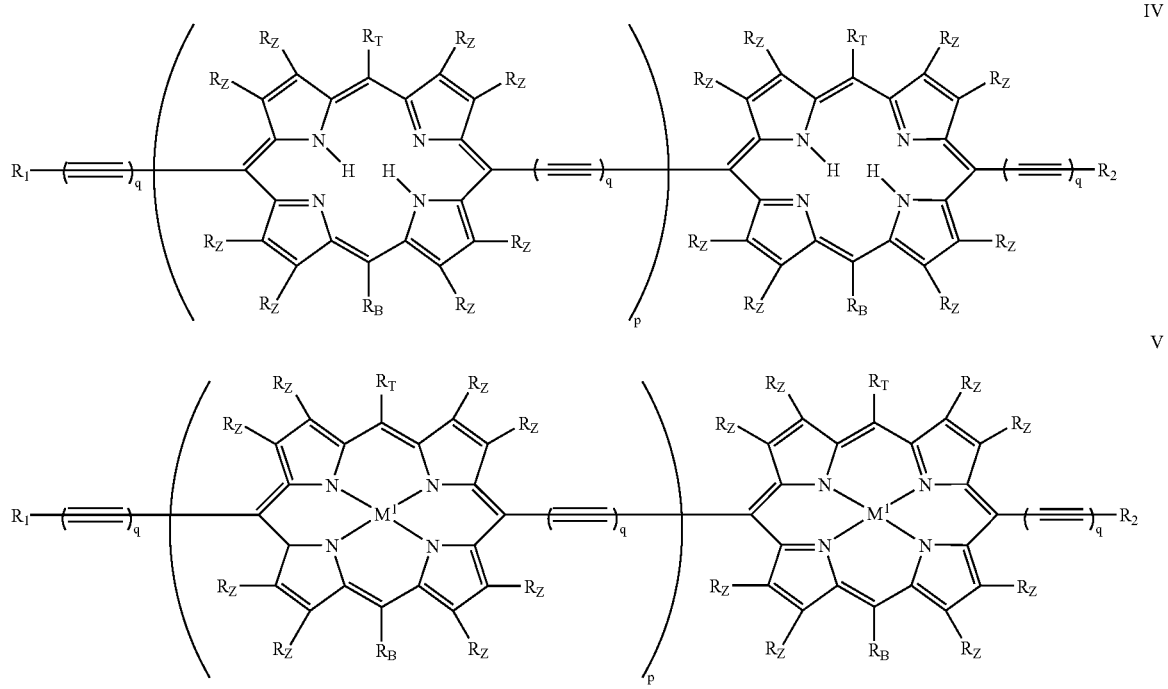

alkenyls having 2 to about 20 carbon atoms; alkynyls having 2 to about 20 carbon atoms, aryls having 3 to about 50 carbon atoms, arylalkynyls having 8 to about 24 carbon atoms, heteroaryls having 2 to about 50 carbon atoms, unsaturated heterocyclos having 4to about 24 carbon atoms, unsaturated heterocycloalkenyls and unsaturated heterocycloalkynyls, wherein each $R_T$ and $R_B$ is optionally substituted; and each $R_Z$ is independently selected from the group consisting of H, electron-donating groups and electron-withdrawing groups.

14. The compound of claim 13 wherein $R_A$ is ethynyl.

15. The compound of claim 13 wherein $M^1$ is zinc.

16. The compound of claim 13 wherein both $R^1$ and $R^2$ are inorganic moieties.

17. The compound of claim 16 wherein $R^1$ and $R^2$ are different inorganic moieties.

18. The compound of claim 13 wherein said inorganic moiety comprises a metal complex comprising a transition metal.

19. The compound of claim 18 wherein said transition metal is a Group 8 metal.

wherein:

$M^1$ is a metal atom;

$R_1$ is selected from the group consisting of H, halo, protecting groups, -organic electron-donating groups, -and inorganic electron-donating moieties and $R_2$ is selected from the group consisting of H, halo, protecting groups, organic electron-accepting groups and inorganic electron-accepting moieties, wherein at least one of $R_1$ and $R_2$ is an inorganic moiety comprising at least one metal atom or metalloid atom, provided said inorganic moiety is not —Pd(Ph$_3$)$_2$Br;

each $R_T$ and $R_B$ is independently selected from the group consisting of -alkyls having 1 to about 20 carbon atoms, alkenyls having 2 to about 20 carbon atoms; alkynyls having 2 to about 20 carbon atoms, aryls having 3 to about 50 carbon atoms, arylalkynyls having 8 to about 24 carbon atoms, heteroaryls having 2 to about 50 carbon atoms, unsaturated heterocyclos having 4 to about 24 carbon atoms, unsaturated heterocycloalkenyls and unsaturated heterocycloalkynyls, wherein each $R_T$ and $R_B$ is optionally substituted;

each $R_Z$ is independently selected from the group consisting of H, -electron-donating groups and electron-withdrawing groups;
p is 0 to 50; and
q is 1 to 5.

25. The compound of claim 24 wherein $M^1$ is zinc.

26. The compound of claim 24 wherein both $R^1$ and $R^2$ are inorganic moieties.

27. The compound of claim 26 wherein $R^1$ and $R^2$ are different inorganic moieties.

28. The compound of claim 24 wherein said inorganic moiety comprises a metal complex comprising a transition metal.

29. The compound of claim 28 wherein said transition metal is a Group 8 metal.

30. The compound of claim 28 wherein said transition metal is selected from the group consisting of Ru, Os, Rh and Pt.

31. The compound of claim 28 wherein said metal complex comprises a polypyridyl ligand.

32. The compound of claim 24 wherein at least one of said $R_T$, $R_B$, or $R_Z$ is a substituent that inhibits aggregation of said compound in the bulk phase.

33. A process for preparing a multichromophoric compound of claim 1, said process comprising, contacting a conjugated macrocycle precursor with an inorganic moiety precursor in the presence of one or more metal-containing catalysts under metal-mediated cross-coupling reaction conditions for a time and under conditions effective to covalently link said conjugated macrocycle precursor with said inorganic moiety precursor to form said multichromophoric compound, wherein said conjugated macrocycle precursor comprises a conjugated macrocycle bearing a first reactive substituent and said inorganic moiety precursor comprises an inorganic moiety bearing a second reactive substituent, and wherein one of either the first or second reactive substituents comprises an organic group selected from alkyl having 1 to about 20 carbon atoms, alkenyl having 2 to about 20 carbon atoms, or alkynyl having 2 to about 20 carbon atoms, aryl having 3 to about 50 carbon atoms, or arylalkynyl having 8 to about 24 carbon atoms, arylalkenyl having 8 to about 24 carbon atoms, unsaturated heterocyclos having 4 to about 24 carbon atoms, heteroaryl having 2 to about 50 carbon atoms, unsaturated heterocycloalkenyls, unsaturated heterocycloalkynyls- and heteroarylalkynyl, and the other of said reactive substituents comprises a leaving group.

34. A process for preparing a multichromophoric compound of claim 13, said process comprising, contacting a conjugated macrocycle precursor with an inorganic moiety precursor in the presence of one or more metal-containing catalysts under metal-mediated cross-coupling reaction conditions for a time and under conditions effective to covalently link said conjugated macrocycle precursor with said inorganic moiety precursor to form said multichromophoric compound, wherein said conjugated macrocycle precursor comprises a conjugated macrocycle bearing a first reactive substituent and said inorganic moiety precursor comprises an inorganic moiety bearing a second reactive substituent, and wherein one of either the first or second reactive substituents comprises an organic group selected from alkyl having 1 to about 20 carbon atoms, alkenyl having 2 to about 20 carbon atoms, or alkynyl having 2 to about 20 carbon atoms, aryl having 3 to about 50 carbon atoms, or arylalkynyl having 8 to about 24 carbon atoms, arylalkenyl having 8 to about 24 carbon atoms, unsaturated heterocyclos having 4 to about 24 carbon atoms, heteroaryl having 2 to about 50 carbon atoms, unsaturated heterocycloalkenyls, unsaturated heterocycloalkynyl and heteroarylalkynyl, and the other of said reactive substituents comprises a leaving group.

35. A process for preparing a multichromophoric compound of claim 24, said process comprising, contacting a conjugated macrocycle precursor with an inorganic moiety precursor in the presence of one or more metal-containing catalysts under metal-mediated cross-coupling reaction conditions for a time and under conditions effective to covalently link said conjugated macrocycle precursor with said inorganic moiety precursor to form said multichromophoric compound, wherein said conjugated macrocycle precursor comprises a conjugated macrocycle bearing a first reactive substituent and said inorganic moiety precursor comprises an inorganic moiety bearing a second reactive substituent, and wherein one of either the first or second reactive substituents comprises an organic group selected from alkyl having 1 to about 20 carbon atoms, alkenyl having 2 to about 20 carbon atoms, or alkynyl having 2 to about 20 carbon atoms, aryl having 3 to about 50 carbon atoms, or arylalkynyl having 8 to about 24 carbon atoms, arylalkenyl having 8 to about 24 carbon atoms, unsaturated heterocyclos having 4 to about 24 carbon atoms, heteroaryl having 2 to about 50 carbon atoms, unsaturated heterocycloalkenyls, unsaturated heterocycloalkynyls and heteroarylalkynyl, and the other of said reactive substituents comprises a leaving group.

36. A composition comprising synthetic organic polymer and at least one compound according to claim 1.

37. The composition of claim 36 wherein said polymer is in admixture with said compound.

38. The composition of claim 36 wherein said polymer is covalently bound with said compound.

39. The composition of claim 36 wherein said polymer is selected from the group consisting of polyimides, polyacrylates, polymethacrylates, polyesters, polycarbonates, polystyrenes, polyolefins, polyvinylethers, polyquinolines, polyurethanes, polyamic acids, fluorocarbon-based polymers, and mixtures thereof.

40. The composition of claim 36 wherein said composition is polarizable or hyperpolarizable.

41. The composition of claim 36 wherein said composition is photorefractive.

42. A method for recording holographic data comprising exposing a composition of claim 41 to an optical intensity pattern representing said holographic data.

43. The method of claim 42 wherein said holographic data comprises a biological image.

44. A composition comprising a synthetic organic polymer and at least one compound according to claim 13.

45. The composition of claim 44 wherein said polymer is in admixture with said compound.

46. The composition of claim 44 wherein said polymer is covalently bound with said compound.

47. The composition of claim 44 wherein said polymer is selected from the group consisting of polyimides, polyacrylates, polymethacrylates, polyesters, polycarbonates, polystyrenes, polyolefins, polyvinylethers, polyquinolines, polyurethanes, polyamic acids, fluorocarbon-based polymers, and mixtures thereof.

48. The composition of claim 44 wherein said composition is polarizable or hyperpolarizable.

49. The composition of claim 44 wherein said composition is photo-refractive.

50. A method for recording holographic data comprising exposing a composition of claim 49 to an optical intensity pattern representing said holographic data.

51. The method of claim 50 wherein said holographic data comprises a biological image.

52. A composition comprising a synthetic organic polymer and at least one compound according to claim 24.

53. The composition of claim 52 wherein said polymer is in admixture with said compound.

54. The composition of claim 52 wherein said polymer is covalently bound with said compound.

55. The composition of claim 52 wherein said polymer is selected from the group consisting of polyimides, polyacrylates, polymethacrylates, polyesters, polycarbonates, polystyrenes, polyolefins, polyvinylethers, polyquinolines, polyurethanes, polyamic acids, fluorocarbon-based polymers, and mixtures thereof.

56. The composition of claim 52 wherein said composition is polarizable or hyperpolarizable.

57. The composition of claim 52 wherein said composition is photo-refractive.

58. A method for recording holographic data comprising exposing a composition of claim 57 to an optical intensity pattern representing said holographic data.

59. The method of claim 58 wherein said holographic data comprises a biological image.

60. A device comprising a substrate and at least one layer on said substrate, said layer comprising a compound of claim 1.

61. The device of claim 60 wherein said substrate is flexible.

62. The device of claim 60 further comprising a superstrate on said layer.

63. The device of claim 60 further comprising means for establishing an electric field across said layer.

64. The device of claim 60 further comprising sensing means for detecting light transmitted by said layer.

65. The device of claim 60 wherein said device is an electro-optic modulator.

66. The device of claim 65 wherein said electro-optic modulator is a high speed modulator for signal processing at optical wavelengths.

67. The device of claim 60 wherein said device is a wave guide.

68. The device of claim 60 wherein said device is a phase shifter.

69. The device of claim 60 wherein said device is an optical limiting device.

70. The device of claim 69 comprising an optical limiting device for optical telecommunications wavelengths.

71. The device of claim 70 wherein said optical telecommunications wavelength is an infrared wavelength.

72. The device of claim 60 wherein said device is a holographic data storage device.

73. The device of claim 60 wherein said device is hermetically sealed.

74. The device of claim 60 wherein said device is a signal processor.

75. The device of claim 60 wherein said device is a frequency boosting device.

76. A device comprising a substrate and at least one layer on said substrate, said layer comprising a compound of claim 13.

77. The device of claim 76 wherein said substrate is flexible.

78. The device of claim 76 further comprising a superstrate on said layer.

79. The device of claim 76 further comprising means for establishing an electric field across said layer.

80. The device of claim 76 further comprising sensing means for detecting light transmitted by said layer.

81. The device of claim 76 wherein said device is an electro-optic modulator.

82. The device of claim 81 wherein said electro-optic modulator is a high speed modulator for signal processing at optical wavelengths.

83. The device of claim 76 wherein said device is a wave guide.

84. The device of claim 76 wherein said device is a phase shifter.

85. The device of claim 76 wherein said device is an optical limiting device.

86. The device of claim 85 comprising an optical limiting device for optical telecommunications wavelengths.

87. The device of claim 86 wherein said optical telecommunications wave-length is an infrared wavelength.

88. The device of claim 76 wherein said device is a holographic data storage device.

89. The device of 76 wherein said device is hermetically sealed.

90. The device of claim 76 wherein said device is a signal processor.

91. The device of claim 76 wherein said device is a frequency boosting device.

92. A device comprising a substrate and at least one layer on said substrate, said layer comprising a compound of claim 24.

93. The device of claim 92 wherein said substrate is flexible.

94. The device of claim 92 further comprising a superstrate on said layer.

95. The device of claim 92 further comprising means for establishing an electric field across said layer.

96. The device of claim 92 further comprising sensing means for detecting light transmitted by said layer.

97. The device of claim 92 wherein said device is an electro-optic modulator.

98. The device of claim 97 wherein said electro-optic modulator is a high speed modulator for signal processing at optical wavelengths.

99. The device of claim 92 wherein said device is a wave guide.

100. The device of claim 92 wherein said device is a phase shifter.

101. The device of claim 92 wherein said device is an optical limiting device.

102. The device of claim 101 comprising an optical limiting device for optical telecommunications wavelengths.

103. The device of claim 102 wherein said optical telecommunications wavelength is an infrared wavelength.

104. The device of claim 92 wherein said device is a holographic data storage device.

105. The device of claim 92 wherein said device is hermetically sealed.

106. The device of claim 92 wherein said device is a signal processor.

107. The device of claim 92 wherein said device is a frequency boosting device.

108. A process for preparing a device, comprising the steps of providing a substrate and placing upon said substrate at least one layer that includes a compound of claim 1.

109. A process for preparing a device, comprising the steps of providing a substrate and placing upon said substrate at least one layer that includes a compound of claim 13.

110. A process for preparing a device, comprising the steps of providing a substrate and placing upon said substrate at least one layer that includes a compound of claim 24.

* * * * *